United States Patent
Lewis et al.

(10) Patent No.: US 10,449,526 B2
(45) Date of Patent: *Oct. 22, 2019

(54) HIGH CHARGE DENSITY METALLOPHOSPHATE MOLECULAR SIEVES

(71) Applicant: UOP LLC, Des Plaines, IL (US)

(72) Inventors: Gregory J. Lewis, Santa Cruz, CA (US); Jaime G. Moscoso, Mount Prospect, IL (US); Lisa M. Knight, Chicago, IL (US); Christopher P. Nicholas, Evanston, IL (US); Seungwan Seo, Gyeongsangnam-do (KR); Junghwan Lee, Gyeonggi-do (KR); Suk Bong Hong, Nam-Gu (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,383

(22) Filed: May 5, 2017

(65) Prior Publication Data

US 2017/0341065 A1 Nov. 30, 2017

Related U.S. Application Data

(60) Provisional application No. 62/341,208, filed on May 25, 2016.

(51) Int. Cl.
| | |
|---|---|
| *C01B 39/54* | (2006.01) |
| *B01J 29/84* | (2006.01) |
| *B01J 37/00* | (2006.01) |
| *B01J 37/04* | (2006.01) |
| *B01J 37/06* | (2006.01) |
| *B01J 37/10* | (2006.01) |
| *B01J 29/72* | (2006.01) |
| *B01J 29/70* | (2006.01) |

(52) U.S. Cl.
CPC ............ *B01J 29/84* (2013.01); *B01J 37/009* (2013.01); *B01J 37/0018* (2013.01); *B01J 37/04* (2013.01); *B01J 37/06* (2013.01); *B01J 37/10* (2013.01); *C01B 39/54* (2013.01); *B01J 29/70* (2013.01); *B01J 29/72* (2013.01); *C01P 2002/74* (2013.01); *Y02P 30/42* (2015.11)

(58) Field of Classification Search
CPC .. C01B 39/54; B01J 29/82; B01J 29/84; B01J 29/72; B01J 29/70; C01P 2002/74
See application file for complete search history.

(56) References Cited

U.S. PATENT DOCUMENTS

| | | | | |
|---|---|---|---|---|
| 1,567,029 A | * | 12/1925 | Borgmann | H04M 5/00 379/313 |
| 4,310,440 A | * | 1/1982 | Wilson | B01J 20/0292 208/112 |
| 4,319,440 A | | 3/1982 | Rassias et al. | |
| 4,440,871 A | * | 4/1984 | Lok | B01J 20/18 208/114 |
| 4,567,029 A | | 1/1986 | Wilson et al. | |
| 4,853,197 A | * | 8/1989 | Wilson | B01J 29/85 423/306 |
| 4,870,222 A | | 9/1989 | Bakas et al. | |
| 5,126,120 A | | 6/1992 | Bedard | |
| 5,126,308 A | | 6/1992 | Barger et al. | |
| 5,152,972 A | | 10/1992 | Gier | |
| 5,157,196 A | | 10/1992 | Crossland et al. | |
| 5,157,197 A | | 10/1992 | Cooper et al. | |
| 5,302,362 A | * | 4/1994 | Bedard | C01B 39/54 423/306 |
| 6,776,975 B2 | | 8/2004 | Wilson et al. | |
| 7,578,993 B2 | | 8/2009 | Lewis et al. | |
| 8,696,886 B1 | | 4/2014 | Lewis et al. | |
| 8,697,927 B1 | | 4/2014 | Lewis et al. | |
| 8,871,177 B2 | | 10/2014 | Lewis et al. | |
| 8,871,178 B2 | | 10/2014 | Lewis et al. | |
| 8,936,776 B2 | * | 1/2015 | Lewis | C01B 39/54 423/277 |
| 10,159,964 B2 | * | 12/2018 | Lewis | C10G 45/04 |
| 10,159,965 B2 | * | 12/2018 | Lewis | B01J 20/048 |

OTHER PUBLICATIONS

Feng et al., Hydrothermal syntheses and structural characterization of zeolite analogue compounds based on cobalt phosphate, Nature, 1997, vol. 388, pp. 735-740. (Year: 1997).*
Xianhui, Large-Cage Zeolite Structures with Multidimensional 12-Ring channels, Science 278, 2080 (1997).
Lin, Hydrothermal Synthesis and Characterization of Two New Microporous Zinc-Substituted Gallium Phosphates Templated by Diaminocyclohexane; Department of Chemistry, National Tsing Hua University, Hsinchu, Taiwan 300, Revised Manuscript.
Park et al., Zeolite Synthesis from a Charge Density Perspective: The Charge Density Mismatch Synthesis of UZM-5 and UZM-9, Chem. Mater. 2014, 26, 6684-6694.
Harrison et. al, Chemistry of materials 1991, 3, 27-29.
Feng, Hydrothermal syntheses and structural characterization of zeolite analogue compounds based on cobalt phosphate, Nature, vol. 388, Aug. 21, 1997.

(Continued)

*Primary Examiner* — David M Brunsman

(57) ABSTRACT

A new family of highly charged crystalline microporous metallophosphate molecular sieves has been synthesized. These metallophosphates are represented by the empirical formula of:

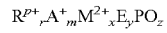

$$R^{p+}_r A^+_m M^{2+}_x E_y PO_z$$

where A is an alkali metal cation, R is at least one quaternary organoammonium cation, M is a divalent metal such as zinc and E is a trivalent framework element such as aluminum or gallium. This family of high charge density metallophosphate materials are among the first metalloalumino(gallo)phosphate-type molecular sieves to be stabilized by combinations of alkali and quaternary organoammonium cations, enabling unique compositions. This family of high charge density metallophosphate molecular sieves has catalytic properties for carrying out various hydrocarbon conversion processes and separation properties for separating at least one component.

7 Claims, 1 Drawing Sheet

(56) References Cited

OTHER PUBLICATIONS

Harrison et. al, Organic Templates in Zincophosphate Synthesis, J. Mater. Chem., 1992, 2(11), 1127-1134.
Cowley et al., CGS: cobalt and zinc gallophosphates with a new open-framework topology, Microporous and Mesoporous Materials 1999, 28, 163-172.
Broach et al., New ABC-6 net molecular sieves ZnAPO-57 and ZnAPO-59: Framework charge density-induced transition from two- to three-dimensional porosity, Microporous and Mesoporous Materials, 189, 2014, 49-63.
Gatter, Stability of framework aluminum in the new zeolite UZM-5, Surface Science, (2004) vol. 154, p. 1324-1331.
Chippindale, CoGaPO-5: Synthesis and crystal structure of $(C_6N_2H_{14})_2[Co_4Ga_5P_9O_{36}]$, a microporous cobalt-gallium phosphate with a novel framework topology, Zeolites 18:176-181, 1997.
Akolekar, Novel, crystalline, large-pore magnesium aluminophosphate molecular sieve of type 50: Preparation, characterization, and structural stability, Zeolites, 1995, 15, 583-590.
Search Report dated Aug. 14, 2017 for corresponding PCT Appl. No. PCT/US2017/031555.

\* cited by examiner

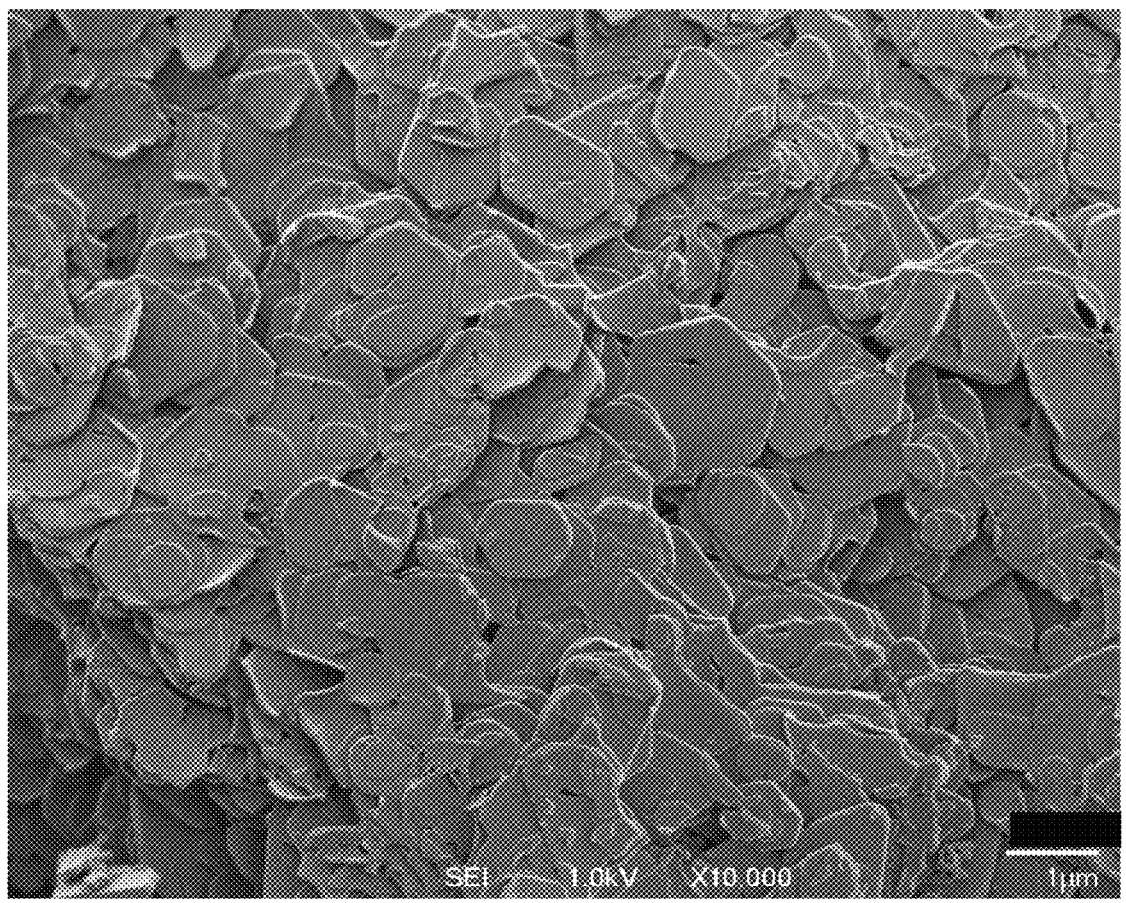

HIGH CHARGE DENSITY METALLOPHOSPHATE MOLECULAR SIEVES

CROSS-REFERENCE TO RELATED APPLICATION

This application claims priority from Provisional Application No. 62/341,208 filed May 25, 2016, the contents of which cited application are hereby incorporated by reference in its entirety.

FIELD OF THE INVENTION

This invention relates to a family of charged metallophosphate-based molecular sieves. They are represented by the empirical formula of:

$$R^{p+}_r A^+_m M^{2+}_x E_y PO_z$$

where A is an alkali metal cation, R is at least one quaternary organoammonium cation, M is a divalent metal such as zinc and E is a trivalent framework element such as aluminum or gallium. This family of high charge density metallophosphate molecular sieves has catalytic properties for carrying out various hydrocarbon conversion processes and separation properties for separating at least one component.

BACKGROUND OF THE INVENTION

Zeolites are crystalline aluminosilicate compositions which are microporous and which are formed from corner sharing $[AlO_{4/2}]^-$ and $SiO_{4/2}$ tetrahedra. Numerous zeolites, both naturally occurring and synthetically prepared are used in various industrial processes. Synthetic zeolites are prepared via hydrothermal synthesis employing suitable sources of Si, Al and structure directing agents (SDAs) such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces of the zeolite as well as on internal surfaces within the pores of the zeolite.

In 1982, Wilson et al. developed aluminophosphate molecular sieves, the so-called AlPOs, which are microporous materials that have many of the same properties of zeolites, but are silica free, composed of $[AlO_{4/2}]^-$ and $[PO_{4/2}]^+$ tetrahedra (See U.S. Pat. No. 4,319,440). Subsequently, charge was introduced to the neutral aluminophosphate frameworks via the substitution of $SiO_{4/2}$ tetrahedra for $[PO_{4/2}]^+$ tetrahedra to produce the SAPO molecular sieves (See U.S. Pat. No. 4,440,871). Another way to introduce framework charge to neutral aluminophosphates is to substitute $[M^{2+}O_{4/2}]^{2-}$ tetrahedra for $[AlO_{4/2}]^-$ tetrahedra, which yield the MeAPO molecular sieves (see U.S. Pat. No. 4,567,029). These MeAPO materials generally showed low substitution levels of $M^{2+}$ for $Al^{3+}$, generally on the order of 10%, while several materials, notably MeAPO-44 exhibited $M^{2+}$ for $Al^{3+}$ substitution levels of 40%. Later, MeAPO-50 also showed nearly 40% substitution of $M^{2+}$ for $Al^{3+}$, but these examples of high $Me^{2+}$ substitution were few (See Zeolites, 1995, 15, 583-590). It is furthermore possible to introduce framework charge on AlPO-based molecular sieves via the introduction both of $SiO_{4/2}$ and $[M^{2+}O_{4/2}]^{2-}$ tetrahedra to the framework, giving MeAPSO molecular sieves (See U.S. Pat. No. 4,973,785).

In the early 1990's, high charge density molecular sieves, similar to the MeAPOs but without the Al, were developed by Bedard (See U.S. Pat. No. 5,126,120) and Gier (See U.S. Pat. No. 5,152,972). These metal phosphates (sometimes arsenates, vanadates) were based on $M^{2+}$ (M=Zn, Co), the general formula of which, in terms of the T-atoms, $T^{2+}$-$T^{5+}$, was approximately $A^+T^{2+}T^{5+}O_4$, having framework charge densities similar to Si/Al=1 zeolites and were charge balanced by alkali cations, $A^+$, in the pores. Later attempts to prepare metallophosphates of similar compositions but with organic SDAs led to porous, but interrupted structures, i.e., the structures contained terminal P—O—H and Zn—N bonds (See J. Mater. Chem., 1992, 2(11), 1127-1134.) Attempts at Al substitution in a zincophosphate network was carried out in the presence of both alkali and organoammonium agents, specifically the most highly charged organoammonium species, tetramethylammonium, but because of the high framework charge density, only the alkali made it into the pores to balance framework charge (See U.S. Pat. No. 5,302,362). Similarly, in a high charge density zincophosphate system that yielded the zinc phosphate analog of zeolite X, the synthesis in the presence of $Na^+$ and $TMA^+$ yielded a product that contained considerably less $TMA^+$ than $Na^+$ (See Chem. Mater., 1991, 3, 27-29).

To bridge the rather large charge density gap between the MeAPOs of U.S. Pat. No. 4,567,029 and the aforementioned alkali-stabilized $Me^{2+}$-phosphates of Bedard and Gier, Stucky's group developed a synthesis route using amines, often diamines in ethylene glycol. They were able to make high charge density, small pore MeAPOs in which the concentrations of $Co^{2+}$ and $Al^{3+}$ in $R(Co_xAl_{1-x})PO_4$ were varied such that $0.33 \leq x \leq 0.9$ in the so-called ACP series of materials, the aluminum cobalt phosphates (See Nature, 1997, 388, 735). Continuing with this synthesis methodology utilizing ethylene glycol-based reaction mixtures and matching the amines to framework charge densities for $R(M^{2+}_xAl_{1-x})PO_4$ such that $0.4 \leq x \leq 0.5$, ($M^{2+}=Mg^{2+}$, $Mn^{2+}$, $Zn^{2+}$, $Co^{2+}$), the large pore materials UCSB-6, -8 and -10 were isolated (See Science, 1997, 278, 2080). Similarly, this approach also yielded MeAPO analogs of zeolite rho of the composition where $RM^{2+}_{0.5}Al_{0.5}PO_4$, where R=N,N'-diisopropyl-1,3-propanediamine, $M^{2+}=Mg^{2+}$, $Co^{2+}$ and $Mn^{2+}$. Cowley followed this ethylene glycol-based approach, which he described as "predominantly non-aqueous solvothermal conditions" to synthesize a high charge density CoGaPO-5, $(DABCO)_2[Co_4Ga_5P_9O_{36}]$, with the DABCO SDA (See Zeolites, 1997, 18, 176-181). Cowley also utilized this strategy to prepare cobalt and zinc gallium phosphates using quinuclidine as the SDA, one of which has the CGS topology with a framework charge density of −0.125/T-atom (See Microporous and Mesoporous Materials 1999, 28, 163-172). Similarly, Lin and Wang used 1,2 diaminocyclohexane (DACH) with the ethylene glycol approach to prepare a Zn—Ga phosphate of CGS topology with higher Zn incorporation than the Cowley work, realizing a framework charge density of −0.25/T-atom for $(H_2DACH)Zn_2Ga_2(PO_4)_4$ (See Chemistry of Materials, 2000, 12, 3617-3623). The reliance of this non-aqueous synthesis approach on ethylene glycol solvent does not lend itself well to industrial scale, from both a safety and environmental point of view.

This non-aqueous approach also leads to very large crystals, often with dimensions of hundreds of microns, which are too large for industrial use, where μ-sized or smaller crystals are often preferred (See Science, 1997, 278, 2080). Other than this work cited here, there has been little activity in this intermediate charge density region, where $0.2 \leq x \leq 0.9$ for the $[M^{2+}{}_xAl_{1-x}PO_4]^{x-}$ compositions.

Pursuing aqueous chemistry, Wright used highly charged triquaternary ammonium SDAs to make new MeAPO materials (See Chem. Mater., 1999, 11, 2456-2462). One of these materials, STA-5 with the BPH topology, $(Mg_{2.1}Al_{11.9}P_{14}O_{28})$, exhibited significant substitution of $Mg^{2+}$ for $Al^{3+}$, up to about 15%, but less substitution than seen in Stucky's non-aqueous ethylene glycol approach.

More recently, Lewis et al. developed aqueous solution chemistry using quaternary ammonium cations leading to high charge density SAPO, MeAPO, and MeAPSO materials, enabling greater substitution of $SiO_{4/2}$ and $[M^{2+}O_{4/2}]^{2-}$ into the framework for $[PO_{4/2}]^+$ and $[AlO_{4/2}]^-$, respectively, using the ethyltrimethylammonium ($ETMA^+$) and diethyldimethylammonium ($DEDMA^+$) SDAs. These materials include ZnAPO-57 (U.S. Pat. No. 8,871,178), ZnAPO-59 (U.S. Pat. No. 8,871,177), ZnAPO-67 (U.S. Pat. No. 8,697,927), and MeAPSO-64 (U.S. Pat. No. 8,696,886). The relationship between the increasing product charge densities and reaction parameters, namely the ETMAOH(DEDMAOH)/$H_3PO_4$ ratios, were outlined in the literature (See Microporous and Mesoporous Materials, 189, 2014, 49-63). In particular, for the metallophosphates, the incorporation of $M^{2+}$ observed in these systems was such that for the formulation $[M^{2+}{}_xAl_{1-x}PO_4]^{x-}$, $x \sim 0.3$.

Applicants have now synthesized a new family of highly charged metallophosphate framework materials with generally higher charge densities than the MeAPOs of U.S. Pat. No. 4,567,029 and the ZnAPO materials isolated by Lewis. These metallophosphates are often prepared from aqueous solution and always use a combination of quaternary ammonium and alkali cations. The utilization of alkali in MeAPO-based systems is uncommon and generally avoided; but in combination with organoammonium cations under the right conditions enables this system to achieve the charge densities and desired midrange compositions between the low charge density MeAPO materials of U.S. Pat. No. 4,567,029 and high charge density $M^{2+}$-phosphate extremes. Furthermore, an aqueous-based approach to high charge density metallophosphates is more scalable and environmentally favorable than the previously known non-aqueous route and this aqueous approach yields crystals of dimensions in the micron to sub-micron range that are more industrially relevant than the large crystals isolated in the non-aqueous approach.

SUMMARY OF THE INVENTION

As stated, the present invention relates to a new family of high charge density metallophosphate molecular sieves. Accordingly, one embodiment of the invention is a microporous crystalline material having a three-dimensional framework of $[M^{2+}O_{4/2}]^{2-}$, $[EO_{4/2}]^-$ and $[PO_{4/2}]^+$ tetrahedral units and an empirical composition in the as synthesized form and anhydrous basis expressed by an empirical formula of:

$$R^{p+}{}_rA^+{}_mM^{2+}{}_xE_yPO_z$$

where R is at least one of any quaternary ammonium cation, diquaternary ammonium cation triquaternary ammonium cation, quatroquaternary ammonium cation and mixtures thereof, "r" is the mole ratio of R to P and has a value of about 0.04 to about 1.0, "p" is the weighted average valence of R and varies from 1 to 4, A is an alkali metal such as $Li^+$, $Na^+$, $K^+$, $Rb^+$ and $Cs^+$ and mixtures thereof, "m" is the mole ratio of A to P and varies from 0.1 to 1.0, M is a divalent element selected from the group of Zn, Mg, Co, Mn and mixtures thereof, "x" is the mole ratio of M to P and varies from 0.2 to about 0.9, E is a trivalent element selected from the group consisting of aluminum and gallium and mixtures thereof, "y" is the mole ratio of E to P and varies from 0.1 to about 0.8 and "z" is the mole ratio of O to P and has a value determined by the equation:

$$z=(m+p \cdot r+2 \cdot x+3 \cdot y+5)/2$$

and the crystalline metallophosphate species is characterized by a specific powder x-ray diffraction pattern.

Another embodiment of the invention is a process for preparing the crystalline metallophosphate molecular sieve described above. The process comprises forming a reaction mixture containing reactive sources of R, A, M, E and P and heating the reaction mixture at a temperature of about 60° C. to about 200° C. for a time sufficient to form the molecular sieve, the reaction mixture having a composition expressed in terms of mole ratios of the oxides of:

$$aR_{2/p}O:bA_2O:cMO:E_2O_3:dP_2O_5:eH_2O$$

where "a" has a value of about 2.1 to about 100, "b" has a value of about 0.1 to about 8.0, "c" has a value of about 0.25 to about 8, "d" has a value of about 1.69 to about 25, and "e" has a value from 30 to 5000.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is a separation process using the crystalline microporous high charge density metallophosphate material. The process may involve separating mixtures of molecular species or removing contaminants by contacting a fluid with the metallophosphate molecular sieve. Separation of molecular species can be based either on the molecular size (kinetic diameter) or on the degree of polarity of the molecular species. Removing contaminants may be by ion exchange with the molecular sieve.

BRIEF DESCRIPTION OF THE DRAWING

The FIGURE shows an analysis of the product by SEM.

DETAILED DESCRIPTION OF THE INVENTION

Applicants have prepared a family of high charge density crystalline microporous metallophosphate compositions, designated HCD MeAPO or HCD metallophosphates. Compared to other early MeAPO materials (U.S. Pat. No. 4,567,029), the HCD MeAPO family of materials generally contains more $M^{2+}$ and exhibits high framework (FW) charge densities that unlike the other MeAPOs, make use of alkali cations in addition to quaternary ammonium ions to balance the FW charge. The instant microporous crystalline materials, the HCD MeAPOs, have an empirical composition in the as-synthesized form and on an anhydrous basis expressed by the empirical formula:

$$R^{p+}{}_rA^+{}_mM^{2+}{}_xE_yPO_z$$

where A is at least one alkali cation and is selected from the group of alkali metals. Specific examples of the A cations include but are not limited to lithium, sodium, potassium, rubidium, cesium and mixtures thereof. R is at least one of any quaternary ammonium cation, diquaternary ammonium cation, triquaternary ammonium cation, quaternary ammonium cation and mixtures thereof and "r" is the mole ratio of R to P and varies from about 0.04 to about 1.0, while "p" is the weighted average valence of R and varies from about 1 to 4. M and E are tetrahedrally coordinated and in the framework, M is a divalent element selected from the group of Zn, Mg, Co, Mn and mixtures thereof, while E is a trivalent element selected from aluminum and gallium and mixtures thereof. The value of "m" is the mole ratio of A to P and varies from 0.1 to about 1.0, "x" is mole ratio of M to P and varies from 0.2 to about 0.9, while the ratio of E to P is represented by "y" which varies from about 0.10 to about 0.8. Lastly, "z" is the mole ratio of O to P and is given by the equation:

$$z=(m+r \cdot p+2 \cdot x+3 \cdot y+5)/2.$$

When only one type of R quaternary ammonium cation is present, then the weighted average valence is just the valence of that cation, e.g., +1 or +2. When more than one R cation is present, the total amount of R is given by the equation:

$$R_r^{p+}=R_{r1}^{(p1)+}+R_{r2}^{(p2)+}+R_{r3}^{(p3)+}+\ldots.$$

the weighted average valence "p" is given by:

$$p = \frac{r1 \cdot p1 + r2 \cdot p2 + r3 \cdot p3 + \ldots}{r1 + r2 + r3 + \ldots}$$

The HCD metallophosphates of this invention are crystalline microporous materials with well-defined pore channels. By "microporous" it is meant that the crystalline HCD MeAPO contains at least one pore system with at least an 8-member ring opening, where an 8-member ring refers to a pore in which 8 T-atoms line the pore circumference; this nomenclature is well-known in the art. That is, the metallophosphates of this invention will exhibit at least one pore with, for example, 8-ring, 10-ring, 12-ring or an even higher number of T-atoms lining the circumference of the pore walls. On the other hand, materials that contain 6-rings are not considered to be porous and are not part of this invention, for example, materials of the SOD topology. When the topology of the metallophosphate is known, as identified by powder x-ray diffraction, the determination of microporosity can be made by consulting the Database of Zeolite structures at (http://izasc.biw.kuleuven.be/fmi/xsl/IZA-SC/ft.xsl). However, when the topology of the metallophosphates of this invention is not known, the determination of microporosity can be made by demonstrating ion-exchange of either the as-synthesized or calcined metallophosphate without significant structural change or by the adsorption of at least a small molecule, such as water or carbon dioxide. These practices are well known in the art.

It has also been noted that in the HCD MeAPO materials of this invention that a portion of $M^{2+}$ may also reside in the pores, likely in a charge balancing role.

The microporous crystalline HCD MeAPO is prepared by a hydrothermal crystallization of a reaction mixture prepared by combining reactive sources of R, A, E, phosphorous and M. A preferred form of the HCD MeAPO materials occurs when E is Al. The sources of aluminum include but are not limited to aluminum alkoxides, precipitated aluminas, aluminum metal, aluminum hydroxide, aluminum salts, alkali aluminates and alumina sols. Specific examples of aluminum alkoxides include, but are not limited to aluminum ortho sec-butoxide and aluminum ortho isopropoxide. Sources of phosphorus include, but are not limited to, orthophosphoric acid, phosphorus pentoxide, and ammonium dihydrogen phosphate. Sources of M include but are not limited to zinc acetate, zinc chloride, cobalt acetate, cobalt chloride, magnesium acetate, magnesium nitrate, manganese sulfate, manganese acetate and manganese nitrate. Sources of the other E elements include but are not limited to precipitated gallium hydroxide, gallium chloride, gallium sulfate or gallium nitrate. Sources of the A metals include the halide salts, nitrate salts, hydroxide salts, acetate salts, and sulfate salts of the respective alkali metals. R is at least one of any organoammonium cation selected from the groups consisting of quaternary ammonium, diquaternary ammonium, triquaternary ammonium, quatroquaternary ammonium cations and mixtures thereof, a few examples of which, but not limited to, are ethyltrimethylammonium ($ETMA^+$), choline, diethydimethylammonium ($DEDMA^+$), trimethylpropylammonium, tetramethylammonium ($TMA^+$), tetraethylammonium ($TEA^+$), tetrapropylammonium ($TPA^+$), hexamethonium ($HM^{2+}$), N,N,N',N'-tetramethyl-N,N'-p-xyleno-1,6-hexanediammonium, N,N,N',N'-tetramethyl-N,N'-butano-1,6-hexanediammonium, tris-1,3,5-(dimethylethylammoniomethyl)benzene, $[(C_6H_5CH_2)(Me_2)N(-CH_2CH(OH)CH_2N(Me_2)-)_3CH_2C_6H_{5}]^{4+}$ and mixtures thereof, and the sources include the hydroxide, chloride, bromide, iodide, acetate and fluoride compounds. Specific examples include without limitation ethyltrimethylammonium hydroxide, ethyltrimethylammonium chloride, diethyldimethylammonium chloride, diethyldimethylammonium hydroxide, propyltrimethylammonium chloride, tetramethylammonium chloride, tetraethylammonium hydroxide, tetrapropylammonium hydroxide, hexamethonium dihydroxide, hexamethonium dichloride, N,N,N',N'-tetramethyl-N,N'-p-xyleno-1,6-hexanediammonium dibromide, N,N,N',N'-tetramethyl-N,N'-butano-1,6-hexanediammonium dihydroxide, tris-1,3,5-(dimethylethylammoniomethyl)benzene tribromide and $[(C_6H_5CH_2)(Me_2)N(-CH_2CH(OH)CH_2N(Me_2)-)_3CH_2C_6H_{5}]^{4+}$ tetrachloride.

The reaction mixture containing reactive sources of the desired components can be described in terms of molar ratios of the oxides by the formula:

$$aR_{2/p}O:bA_2O:cMO:E_2O_3:dP_2O_5:eH_2O$$

where "a" varies from about 2.1 to about 100, "b" varies from about 0.1 to about 8, "c" varies from about 0.25 to about 8, "d" varies from about 1.69 to about 25, and "e" varies from 30 to 5000. If alkoxides are used, it is preferred to include a distillation or evaporative step to remove the alcohol hydrolysis products. The reaction mixture is now reacted at a temperature of about 60° C. to about 200° C. and preferably from about 125° C. to about 175° C. for a period of about 1 day to about 3 weeks and preferably for a time of about 1 day to about 7 days in a sealed reaction vessel at autogenous pressure. After crystallization is complete, the solid product is isolated from the heterogeneous mixture by means such as filtration or centrifugation, and then washed with deionized water and dried in air at ambient temperature up to about 100° C. HCD MeAPO seeds can optionally be added to the reaction mixture in order to accelerate or otherwise enhance the formation of the desired microporous composition.

A favored approach for the synthesis of HCD metallophosphates is the Charge Density Mismatch Approach, which has been applied to the synthesis of aluminosilicate zeolites (See U.S. Pat. No. 7,578,993 and Chem. Mater., 2014, 26, 6684-6694). It is applied to high charge density metallophosphates (HCD MeAPOs) for the first time here. Metalloalumino(gallo)phosphate solutions are prepared with excess phosphate and large, low charge density SDAs, such as TPAOH, TEAOH, and TBAOH, which are then perturbed by the addition of small amounts of alkali and more highly charged organoammonium cations, including quaternary ammonium, diquaternary ammonium, cyclic diquaternary ammonium, triquaternary ammonium and quatroquaternary ammonium cations to induce crystallization under the synthesis conditions. This leads to rich chemistry in which there is often cooperation between multiple SDAs to form one molecular sieve structure. The method has advantages in expense and efficiency because non-commercially available organoammonium cations, for instance, the cyclic diquaternary organoammonium cations used in MeAPO-81 synthesis presented herein, can be utilized in small amounts as halide salts; they don't have to be converted to the hydroxide form for use, an additional and expensive step.

The various crystalline microporous HCD metallophosphates, which are obtained from the above-described process, are characterized by a specific x-ray diffraction patterns, as illustrated in the examples.

The HCD metallophosphates may be modified in many ways to tailor it for use in a particular application. Modifications include calcination, ammonia calcinations, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. In addition, properties that may be modified include porosity, adsorption, framework composition, acidity, thermal stability, etc.

As synthesized, the HCD metallophosphate materials will contain some exchangeable or charge balancing cations in its pores. These exchangeable cations can be exchanged for other cations, or in the case of organic cations, they can be removed by heating under controlled conditions. Some HCD metallophosphates are large pore materials, for instance with 12-ring pores, and many organic cations may be removed directly by ion-exchange, heating may not be necessary. If heating is required to remove organoammonium cations from the pores, a preferred method is ammonia calcination. Calcination in air converts the organic cations in the pores to protons, which can lead to the loss of some metal, for example Al, from the framework upon exposure to ambient atmospheric water vapor. When the calcination is carried out in an ammonia atmosphere, the organic cation in the pore is replaced by $NH_4^+$ cation and the framework remains intact (See Studies in Surface Science, (2004) vol. 154, p. 1324-1331). Typical conditions for ammonia calcinations include the use of gaseous anhydrous ammonia flowing at a rate of 1.1 l/min while ramping the sample temperature at 5° C./min to 500° C. and holding at that temperature for a time ranging from 5 minutes to an hour. Once in this form, the ammonia calcined material may be ion-exchanged with $H^+$, $NH_4^+$, alkali metals, alkaline earth metals, transition metals, rare earth metals, or any mixture thereof, to achieve a wide variety of compositions with the HCD metallophosphate framework in superior condition.

When HCD metallophosphates or their modified forms are calcined in air, there can be a loss of metal from the framework, such as Al, which can alter the x-ray diffraction pattern from that observed for the as-synthesized form (See Studies in Surface Science, (2004) vol. 154, p. 1324-1331).

Typical conditions for the calcination of the HCD metallophosphate sample include ramping the temperature from room temperature to a calcination temperature of 400-600° C., preferably a calcination temperature of 450-550° C. at a ramp rate of 1 to 5° C./min, preferably a ramp rate of 2 to 4° C./min, the temperature ramp conducted in an atmosphere consisting either of flowing nitrogen or flowing clean dry air, preferably an atmosphere of flowing nitrogen. Once at the desired calcination temperature, if the calcination atmosphere employed during the temperature ramp is flowing clean dry air, it may remain flowing clean dry air. If the calcination atmosphere during the ramp was flowing nitrogen, it may remain flowing nitrogen at the calcination temperature or it may be immediately converted to clean dry air; preferably at the calcination temperature the calcination atmosphere will remain flowing nitrogen for a period of 1-10 hr and preferably for a period of 2-4 hours before converting the calcination atmosphere to flowing clean dry air. The final step of the calcination is a dwell at the calcination temperature in clean dry air. Whether the calcination atmosphere during the initial temperature ramp was flowing nitrogen or flowing clean dry air, once at the calcination temperature and once the calcination atmosphere is clean dry air, the HCD metallophosphate sample will spend a period of 1-24 hr and preferably a period of 2-6 hr under these conditions to complete the calcination process.

The crystalline HCD metallophosphate materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The HCD metallophosphate compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. Nos. 4,310,440, 4,440,871 and 5,126,308, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (178-8,888 std. $m^3/m^3$), preferably between 2,000 and 30,000 scf per barrel of charge (355-5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the HCD metallophosphate composition using feedstocks such as gas oils, heavy naphthas, deasphalted crude oil residua, etc. with gasoline being the principal desired product. Temperature conditions of 850° to 1100° F. (455° C. to 593° C.), LHSV values of 0.5 $hr^{-1}$ to 10 $hr^{-1}$ and pressure conditions of from about 0 to 50 psig (0-345 kPa) are suitable.

Alkylation of aromatics usually involves reacting an aromatic ($C_2$ to $C_{12}$), especially benzene, with a monoolefin to produce a linear alkyl substituted aromatic. The process is carried out at an aromatic: olefin (e.g., benzene:olefin) ratio of between 5:1 and 30:1, a LHSV of about 0.3 to about 6 $hr^{-1}$, a temperature of about 100° to about 250° C. and pressures of about 200 to about 1000 psig (1,379-6,895 kPa). Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 $hr^{-1}$ to about 120 $hr^{-1}$. Details on paraffin alkylation may be found in U.S. Pat. Nos. 5,157,196 and 5,157,197, which are incorporated by reference.

The conversion of methanol to olefins is effected by contacting the methanol with the HCD metallophosphate catalyst at conversion conditions, thereby forming the desired olefins. The methanol can be in the liquid or vapor phase with the vapor phase being preferred. Contacting the methanol with the HCD metallophosphate catalyst can be done in a continuous mode or a batch mode with a continuous mode being preferred. The amount of time that the methanol is in contact with the HCD metallophosphate catalyst must be sufficient to convert the methanol to the desired light olefin products. When the process is carried out in a batch process, the contact time varies from about 0.001 hrs to about 1 hr and preferably from about 0.01 hr to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e. g., methane, aromatic hydrocarbons, e. g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the HCD metallophosphate catalyst. When multiple reaction zones are used, one or more HCD metallophosphate catalysts may be used in series to produce the desired product mixture. Instead of a fixed bed, a dynamic bed system, e. g., fluidized or moving, may be used. Such a dynamic system would facilitate any regeneration of the HCD metallophosphate catalyst that may be required. If regeneration is required, the HCD metallophosphate catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims. The products of this invention are designated with names, where the suffix, always a numeral, will refer to a particular molecular sieve topology, as indicated in each example.

The structure of the HCD metallophosphate compositions of this invention was determined by x-ray analysis. The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100× $I/I_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

A Teflon beaker was charged with 150.00 g ETMAOH (20% aqueous, SACHEM Inc.) and placed under a high speed stirring apparatus. Pre-ground aluminum isopropoxide (13.3% Al), 4.82 g, was added to the reaction mixture and dissolved with stirring. This was followed by the dropwise addition of 16.31 g $H_3PO_4$ (85.7%). Separately, 5.22 g $Zn(OAc)_2 \cdot 2H_2O$ was dissolved in 20.50 g de-ionized water and the resulting solution was added to the reaction mixture in a dropwise fashion. After completion of the addition, the reaction mixture was homogenized for an hour. Then, a solution was prepared by dissolving 1.17 g KOAc (99.4%) in 10.00 g de-ionized water. This was added to the reaction mixture in a dropwise fashion and the reaction mixture was homogenized for an additional 20 minutes post-addition. The reaction mixture was distributed among 7 Teflon-lined autoclaves and digested quiescently at autogenous pressures at temperatures of 95, 125, 150, and 175° C., for either 40 or 167 hr or both. The solid products were isolated by centrifugation and washed with de-ionized water. All of the products were identified as PST-17, which has the BPH topology, by powder x-ray diffraction, except for the product 175° C./167 hr digestion, which also contained a significant impurity. The representative diffraction lines are shown in Table 1 below for the sample from the 125° C./167 hr digestion. Elemental analysis of this same product showed it was composed of the elemental ratios Al/P=0.31, Zn/P=0.70, K/P=0.37, and N/P=0.21, consistent with the stoichiometry $ETMA_{0.21}K_{0.37}Zn_{0.70}Al_{0.31}P$.

TABLE 1

| 2-Θ | d(Å) | I/I₀(%) |
|---|---|---|
| 6.69 | 13.19 | vs |
| 7.54 | 11.72 | m |
| 13.10 | 6.76 | w |
| 13.40 | 6.60 | w |
| 14.701 | 6.02 | w |
| 15.39 | 5.75 | w |
| 18.76 | 4.73 | w |
| 20.14 | 4.41 | m |
| 21.14 | 4.20 | m |
| 23.75 | 3.74 | w |
| 24.08 | 3.69 | m |
| 26.50 | 3.36 | w |
| 27.20 | 3.28 | w |
| 27.43 | 3.25 | w |
| 28.26 | 3.16 | w |
| 28.56 | 3.12 | w |
| 29.66 | 3.01 | m |
| 30.08 | 2.97 | m |
| 30.52 | 2.93 | w |
| 31.06 | 2.88 | w |
| 31.26 | 2.86 | w |
| 33.31 | 2.69 | w |
| 33.82 | 2.65 | w |
| 34.25 | 2.62 | w |
| 35.08 | 2.56 | w |
| 35.74 | 2.51 | w |
| 36.48 | 2.46 | w |
| 38.02 | 2.36 | w |
| 38.85 | 2.32 | w |
| 39.21 | 2.30 | w |
| 39.72 | 2.27 | w |
| 40.76 | 2.21 | w |
| 42.98 | 2.10 | w |
| 43.42 | 2.08 | w |

TABLE 1-continued

| 2-Θ | d(Å) | I/I₀(%) |
|---|---|---|
| 47.37 | 1.92 | w |
| 48.84 | 1.86 | w |
| 49.54 | 1.84 | w |
| 50.14 | 1.82 | w |
| 51.10 | 1.79 | w |
| 53.06 | 1.72 | w |
| 53.38 | 1.72 | w |
| 53.96 | 1.70 | w |
| 55.60 | 1.65 | w |

Example 2

A Teflon beaker was charged with 174.00 g diethyldimethylammonium hydroxide (DEDMAOH, 20% aqueous, SACHEM, Inc.) and placed under a high speed mixer. Pre-ground aluminum isopropoxide (13.2% Al), 4.97 g, was added to the reaction mixture and stirred until dissolved. This was followed by the dropwise addition of 16.69 g $H_3PO_4$ (85.7%). Separately, $Zn(OAc)_2 \cdot 2H_2O$, 5.34 g, was dissolved in 25.00 g de-ionized water. This solution was added dropwise to the reaction mixture with vigorous stirring to homogenize. An additional solution was prepared by dissolving KOAc (99.4%), 1.19 g, in 12.88 g de-ionized water. This solution was added dropwise to the reaction mixture and stirred for an hour. The reaction mixture was distributed among 7 Teflon-lined autoclaves and digested quiescently at autogenous pressures at temperatures of 95, 125, 150, and 175° C., for either 48, 136 hr, or 170 hr. The solid products were isolated by centrifugation and washed with de-ionized water. With the exception of the product of the 95° C./170 hr digestion, all of the products were found to contain PST-17, which has the BPH topology, by powder x-ray diffraction. The representative diffraction lines are shown in Table 2 below for the PST-17 products from the 125° C./48 hr (Table 2a) and 175° C./136 hr (Table 2b) digestions. Elemental analysis of these same products showed they were composed of the following elemental ratios, 125° C./48 hr: Al/P=0.36, Zn/P=0.75, K/P=0.36, and N/P=0.25, consistent with the stoichiometry $DEDMA_{0.25}K_{0.36}Zn_{0.75}Al_{0.36}P$ and 175° C./136 hr: Al/P=0.39, Zn/P=0.60, K/P=0.26, and N/P=0.31, consistent with the stoichiometry $DEDMA_{0.31}K_{0.26}Zn_{0.60}Al_{0.39}P$.

TABLE 2

| Table 2a | | | Table 2b | | |
|---|---|---|---|---|---|
| 2-Θ | d(Å) | I/I₀(%) | 2-Θ | d(Å) | I/I₀(%) |
| 6.70 | 13.19 | vs | 6.72 | 13.14 | s |
| 7.54 | 11.72 | s | 7.56 | 11.69 | vs |
| 13.06 | 6.77 | w | 10.11 | 8.75 | w |
| 13.40 | 6.60 | w | 13.11 | 6.75 | w |
| 14.71 | 6.02 | w | 13.44 | 6.58 | w |
| 15.40 | 5.75 | m | 14.74 | 6.01 | w |
| 18.76 | 4.73 | m | 15.44 | 5.74 | m |
| 20.02 | 4.43 | w | 16.56 | 5.35 | w |
| 20.18 | 4.40 | m | 18.76 | 4.72 | m |
| 21.12 | 4.20 | m | 20.22 | 4.39 | m |
| 23.73 | 3.75 | w | 21.18 | 4.19 | m |
| 24.12 | 3.69 | m | 23.78 | 3.74 | w |
| 26.32 | 3.38 | w | 24.18 | 3.68 | m |
| 26.48 | 3.36 | w | 26.54 | 3.36 | m |
| 27.18 | 3.28 | w | 27.24 | 3.27 | m |
| 27.42 | 3.25 | w | 27.44 | 3.25 | w |
| 28.24 | 3.16 | w | 28.28 | 3.15 | m |
| 28.56 | 3.12 | w | 28.64 | 3.11 | m |

TABLE 2-continued

| Table 2a | | | Table 2b | | |
|---|---|---|---|---|---|
| 2-Θ | d(Å) | I/I₀(%) | 2-Θ | d(Å) | I/I₀(%) |
| 29.64 | 3.01 | m | 29.70 | 3.01 | m |
| 30.12 | 2.96 | m | 30.18 | 2.96 | m |
| 30.58 | 2.92 | m | 30.64 | 2.92 | m |
| 31.08 | 2.88 | w | 31.20 | 2.86 | w |
| 31.22 | 2.86 | w | 33.36 | 2.68 | m |
| 33.28 | 2.69 | w | 33.90 | 2.64 | m |
| 33.84 | 2.65 | m | 34.36 | 2.61 | w |
| 34.27 | 2.61 | w | 35.14 | 2.55 | w |
| 35.04 | 2.56 | w | 35.73 | 2.51 | w |
| 35.72 | 2.51 | w | 36.08 | 2.49 | w |
| 36.50 | 2.46 | w | 36.58 | 2.45 | w |
| 38.09 | 2.36 | w | 38.14 | 2.36 | w |
| 39.22 | 2.30 | w | 38.93 | 2.31 | w |
| 39.72 | 2.27 | w | 39.82 | 2.26 | w |
| 39.96 | 2.25 | w | 40.84 | 2.21 | w |
| 40.78 | 2.21 | w | 42.97 | 2.10 | w |
| 41.29 | 2.18 | w | 43.54 | 2.08 | w |
| 42.92 | 2.11 | w | 44.10 | 2.05 | w |
| 43.46 | 2.08 | w | 44.33 | 2.04 | w |
| 44.20 | 2.05 | w | 47.53 | 1.91 | w |
| 46.45 | 1.95 | w | 48.38 | 1.88 | w |
| 48.88 | 1.86 | w | 48.98 | 1.86 | w |
| 49.52 | 1.84 | w | 49.56 | 1.84 | w |
| 50.18 | 1.82 | w | 50.33 | 1.81 | w |
| 51.04 | 1.79 | w | 51.14 | 1.78 | w |
| 53.02 | 1.73 | w | 53.12 | 1.72 | w |
| 53.37 | 1.72 | w | 53.48 | 1.71 | w |
| 53.93 | 1.70 | w | 54.10 | 1.69 | w |
| 55.24 | 1.66 | w | 55.30 | 1.66 | w |
| 55.69 | 1.65 | w | | | |

Example 3

A Teflon bottle was charged with 159.12 g ETMAOH (20%) followed by the addition of 6.31 g of Al-isopropoxide (Al(OiPr)$_3$, 98+%, Sigma-Aldrich). The mixture was stirred in a sealed bottle until the Al(OiPr)$_3$ was fully dissolved. The mixture was transferred to a Teflon beaker equipped with an overhead high speed stirrer. Then, H$_3$PO$_4$ (85%), 20.95 g, was added slowly with vigorous mixing. Separately, 6.78 g zinc acetate dihydrate was dissolved in 30 g of deionized water. The Zn solution was then slowly added to the Al/P/ETMAOH solution over a period of 30 min while mixing continued. Homogenization of the reaction mixture was continued for 30 min after completion of the Zn addition. In a separate beaker, 1.82 g KBr was dissolved in 25.03 g deionized water. This was then added slowly to the reaction mixture while continuing to mix. Again, mixing was continued for 30 min after this addition was completed. A clear solution reaction mixture was then distributed between 4×125 ml Teflon-lined autoclaves and digested quiescently for 7 and 8 d at 150° C. at autogenous pressure. The solid products were isolated by centrifugation and washed with de-ionized water. Powder X-ray diffraction showed all of the products to be PST-17 with the BPH topology. Representative diffraction lines for the PST-17 product are given in Table 3 below.

TABLE 3

| 2Θ | d(Å) | I/I₀ % |
|---|---|---|
| 6.83 | 12.94 | vs |
| 7.69 | 11.49 | m |
| 10.24 | 8.63 | w |
| 13.24 | 6.68 | w |
| 13.55 | 6.53 | w |
| 14.87 | 5.95 | w |
| 15.55 | 5.70 | w |
| 18.92 | 4.69 | w |
| 20.30 | 4.37 | w |
| 21.32 | 4.16 | w |
| 23.91 | 3.72 | w |
| 24.27 | 3.66 | m |
| 26.66 | 3.34 | w |
| 27.38 | 3.25 | w |
| 27.60 | 3.23 | w |
| 28.46 | 3.13 | w |
| 28.76 | 3.10 | w |
| 29.84 | 2.99 | w |
| 30.26 | 2.95 | m |
| 30.77 | 2.90 | w |
| 31.27 | 2.86 | w |
| 31.43 | 2.84 | w |
| 33.51 | 2.67 | w |
| 34.02 | 2.63 | w |
| 35.26 | 2.54 | w |
| 36.68 | 2.45 | w |
| 38.24 | 2.35 | w |
| 39.85 | 2.26 | w |
| 40.14 | 2.24 | w |
| 40.97 | 2.20 | w |
| 43.22 | 2.09 | w |
| 43.62 | 2.07 | w |

Example 4 Ion-Exchange of PST-17

A Na$^+$ ion-exchange was carried out on the product from the 7 d at 150° C. reaction in Example 3. A 1.75 g portion of the dried PST-17 was slurried in 29.2 g of a 6% NaCl solution. The slurry was covered and heated to 75° C. while mixing on a stir plate. The slurry was held at 75° C. for ~1 h. The solid was then collected and washed with deionized water. This process was repeated two additional times. The solid was dried at 100° C. after the final exchange step. A Leco CHN analysis showed that the C level was reduced to 2.75 wt % after the exchange, where typically as-synthesized PST-17 contains 6.5-11% carbon. This shows that significant portion of the organic cation may be removed directly by ion-exchange.

Example 5 NH$_4^+$ Ion-Exchange of PST-17

A Teflon bottle was charged with 891.07 g ETMAOH (20%, SACHEM, Inc.). A 35.31 g portion of aluminum isopropoxide (AIP, 98+%) was added and the mixture was stirred in the sealed bottle until the AIP was fully dissolved. The reaction mixture was transferred to a Teflon beaker and 117.32 g of H$_3$PO$_4$ (85%) was added slowly while mixing with an overhead stirrer. Separately, 37.95 g of zinc acetate dehydrate was dissolved in 168.00 g of deionized water. The zinc acetate solution was then slowly added to the reaction mixture over a period of 2 hours, while mixing with an overhead stirrer. The mixing was continued for 30 min after the addition was completed. In a separate beaker, 10.18 g KBr was dissolved in 25.03 g deionized water. This was then added slowly to the reaction mixture while continuing to mix with an overhead stirrer. The mixing was continued for 30 min after this addition was complete. A slightly hazy solution resulted. The solution was then transferred to a 2 L autoclave and digested for 7 days at 150° C. at autogenous pressure. The product was isolated by centrifugation, washed with deionized water and dried at 100° C. Powder x-ray diffraction showed the product to be PST-17 with the BPH topology. Representative diffraction lines for the PST-17 product are shown in Table 4a below. Elemental analysis showed the PST-17 to consist of the following elemental ratios: Al/P=0.32, Zn/P=0.71, K/P=0.37, and N/P=0.25, consistent with the empirical formula $ETMA_{0.25}K_{0.37}Zn_{0.71}Al_{0.32}P$. Specifically, the carbon content in this PST-17 was 7.56%.

A 20 g portion of the as-synthesized PST-17 material was then ammonium ion-exchanged. A 20 g portion of $NH_4NO_3$ was dissolved in 200 g deionized water. The dried PST-17 material was then added to this solution while mixing on a magnetic stir plate. The slurry was covered and heated to 75° C. for 1.5 hours. The solid was collected and washed by filtration. The exchange procedure was repeated two additional times. The solid was dried at 100° C. after the final exchange step. The ammonium ion-exchanged PST-17 was identified as such by powder x-ray diffraction; the representative diffraction lines shown in table 4b below. Leco CHN analysis showed that the carbon content in the ammonium ion-exchanged PST-17 is 0.21%, indicating that more than 97% of the ETMA+SDA had been removed by ion-exchange.

TABLE 4

| Table 4a | | | Table 4b | | |
|---|---|---|---|---|---|
| 2-Θ | d(Å) | I/I₀ % | 2-Θ | d(Å) | I/I₀ % |
| 6.72 | 13.15 | vs | 6.73 | 13.12 | vs |
| 7.58 | 11.65 | m | 7.61 | 11.61 | s |
| 10.13 | 8.72 | w | 10.15 | 8.71 | w |
| 13.14 | 6.73 | w | 13.19 | 6.71 | w |
| 13.45 | 6.58 | w | 13.46 | 6.57 | m |
| 14.76 | 6.00 | w | 14.81 | 5.98 | w |
| 15.44 | 5.73 | w | 15.47 | 5.72 | w |
| 16.60 | 5.34 | w | 18.86 | 4.70 | w |
| 18.82 | 4.71 | w | 20.22 | 4.39 | w |
| 20.20 | 4.39 | w | 21.29 | 4.17 | m |
| 21.21 | 4.18 | w | 23.89 | 3.72 | w |
| 22.84 | 3.89 | w | 24.21 | 3.67 | m |
| 24.16 | 3.68 | m | 26.63 | 3.35 | w |
| 26.58 | 3.35 | w | 27.08 | 3.29 | w |
| 27.27 | 3.27 | w | 27.38 | 3.25 | w |
| 27.51 | 3.24 | w | 27.62 | 3.23 | w |
| 28.35 | 3.15 | w | 28.44 | 3.14 | w |
| 28.63 | 3.12 | w | 28.68 | 3.11 | w |
| 29.74 | 3.00 | w | 29.82 | 2.99 | m |
| 30.15 | 2.96 | m | 30.19 | 2.96 | m |
| 30.63 | 2.92 | w | 30.71 | 2.91 | w |
| 31.34 | 2.85 | w | 31.16 | 2.87 | w |
| 33.41 | 2.68 | w | 31.41 | 2.85 | w |
| 33.90 | 2.64 | w | 33.53 | 2.67 | w |
| 35.16 | 2.55 | w | 33.96 | 2.64 | w |
| 35.84 | 2.50 | w | 34.23 | 2.62 | w |
| 36.53 | 2.46 | w | 34.44 | 2.60 | w |
| 38.12 | 2.36 | w | 35.30 | 2.54 | w |
| 38.93 | 2.31 | w | 36.60 | 2.45 | w |
| 39.34 | 2.29 | w | 38.21 | 2.35 | w |
| 39.78 | 2.26 | w | 39.83 | 2.26 | w |
| 40.85 | 2.21 | w | 40.93 | 2.20 | w |
| 43.07 | 2.10 | w | 43.19 | 2.09 | w |
| 43.48 | 2.08 | w | 43.58 | 2.07 | w |
| 44.25 | 2.05 | w | 46.14 | 1.97 | w |
| 46.02 | 1.97 | w | 49.77 | 1.83 | w |
| 46.57 | 1.95 | w | 51.36 | 1.78 | w |
| 48.97 | 1.86 | w | 53.32 | 1.72 | w |
| 49.62 | 1.84 | w | 55.70 | 1.65 | w |
| 50.21 | 1.82 | w | | | |
| 50.66 | 1.80 | w | | | |
| 51.18 | 1.78 | w | | | |
| 51.69 | 1.77 | w | | | |
| 53.15 | 1.72 | w | | | |
| 53.44 | 1.71 | w | | | |
| 54.04 | 1.70 | w | | | |

Example 6

A Teflon beaker was charged with 150 g ethyltrimethylammonium hydroxide (ETMAOH, 20%, SACHEM Inc.) and placed under a high speed stirrer. Aluminum isopropoxide (Al(OiPr)₃, 13.3% Al, Sigma-Aldrich) was pre-ground in a mortar and 5.79 g was dissolved in the ETMAOH solution with stirring. This was followed by the dropwise addition of 19.57 g $H_3PO_4$ (85.7%, Sigma-Aldrich). The reaction mixture was allowed to stir. Separately, 6.26 g Zn(OAc)₂*2H₂O was dissolved in 25.00 g de-ionized water. This solution was added dropwise to the reaction mixture. Then 1.06 g KCl was dissolved in 35.00 g de-ionized water and added dropwise to the reaction mixture with stirring. The reaction mixture was distributed among 7 Teflon-lined autoclaves and digested quiescently at 95, 125, 150, and 175° C. at autogenous pressure for 44 and 165 hr. The solid products were isolated by centrifugation and washed with de-ionized water. The products from the 95, 125 and 150° C. digestions were identified as PST-16, which has the CGS topology, by powder x-ray diffraction, while the 175° C. digestions yielded PST-17 samples (BPH topology) with impurities. Table 5 below shows the representative diffraction lines for the PST-16 product resulting from the 150° C./44 hr digestion. Elemental analysis showed this PST-16 product was composed of the elemental ratios C/N=5.31, Al/P=0.51, Zn/P=0.53, K/P=0.25 and N/P=0.23, consistent with the stoichiometry $ETMA_{0.23}K_{0.25}Zn_{0.53}Al_{0.51}P$.

TABLE 5

| 2-Θ | d(Å) | I/I₀(%) |
|---|---|---|
| 8.20 | 10.78 | vs |
| 10.72 | 8.24 | w |
| 11.56 | 7.65 | w |
| 12.38 | 7.14 | m |
| 13.02 | 6.80 | w |
| 13.25 | 6.68 | w |
| 16.42 | 5.39 | s |
| 16.81 | 5.27 | w |
| 17.17 | 5.16 | w |
| 19.16 | 4.63 | m |
| 19.40 | 4.57 | m |
| 19.54 | 4.54 | m |
| 21.30 | 4.17 | w |
| 21.56 | 4.12 | m |
| 21.76 | 4.08 | m |
| 22.18 | 4.00 | m |
| 22.72 | 3.91 | w |
| 23.00 | 3.86 | w |
| 23.26 | 3.82 | w |
| 23.72 | 3.75 | w |
| 24.10 | 3.69 | m |
| 24.798 | 3.59 | w |
| 26.26 | 3.39 | w |
| 26.68 | 3.34 | w |
| 27.22 | 3.27 | m |
| 27.92 | 3.19 | m |
| 28.92 | 3.08 | m |
| 29.34 | 3.04 | m |
| 30.34 | 2.94 | w |
| 30.66 | 2.91 | w |
| 31.48 | 2.84 | m |
| 31.78 | 2.81 | m |
| 33.18 | 2.70 | w |
| 34.20 | 2.62 | w |

Example 7

A Teflon beaker was charged with 150.00 g ETMAOH (20%) and placed under a high speed stirrer. Aluminum isopropoxide (13.3% Al) was pre-ground in a mortar. The Al(OiPr)$_3$, 5.79 g, was then dissolved in the stirring ETMAOH solution. This was followed by the dropwise addition of 19.57 g H$_3$PO$_4$ (85.7%), again with stirring. Separately, 6.26 g Zn(OAc)$_2$*2H$_2$O was dissolved in 30.03 g de-ionized water and added fast dropwise to the stirring reaction mixture. Then 2.82 g KOAc (99.4%) was dissolved in 30.10 g de-ionized water and added dropwise to the reaction mixture. The reaction mixture was distributed among 7 Teflon-lined autoclaves and digested quiescently at autogenous pressures at temperatures of 95, 125, 150, and 175° C., for either 46 or 165 hr or both. The solid products were isolated by centrifugation and washed with de-ionized water. The sample from the 95° C./165 hr digestion was identified as PST-16, which has the CGS topology, by powder x-ray diffraction, the representative diffraction lines of which are shown in Table 6 below. Elemental analysis showed this PST-16 product was composed of the elemental ratios C/N=5.06, Al/P=0.43, Zn/P=0.60, K/P=0.41, and N/P=0.16, consistent with the stoichiometry ETMA$_{0.16}$K$_{0.41}$Zn$_{0.60}$Al$_{0.43}$P.

TABLE 6

| 2-Θ | d(Å) | I/I$_0$(%) |
|---|---|---|
| 8.20 | 10.78 | vs |
| 10.74 | 8.23 | w |
| 11.54 | 7.66 | m |
| 12.38 | 7.14 | s |
| 13.02 | 6.80 | w |
| 13.22 | 6.69 | w |
| 16.44 | 5.39 | m |
| 16.78 | 5.28 | w |
| 17.16 | 5.16 | w |
| 17.56 | 5.05 | w |
| 19.14 | 4.63 | m |
| 19.56 | 4.54 | m |
| 20.54 | 4.32 | w |
| 21.58 | 4.11 | m |
| 21.78 | 4.08 | m |
| 22.18 | 4.00 | m |
| 22.74 | 3.91 | w |
| 23.02 | 3.86 | m |
| 23.24 | 3.82 | w |
| 23.74 | 3.75 | w |
| 24.10 | 3.69 | m |
| 24.82 | 3.58 | m |
| 26.24 | 3.39 | m |
| 26.66 | 3.34 | w |
| 27.24 | 3.27 | s |
| 27.82 | 3.20 | m |
| 28.94 | 3.08 | s |
| 29.34 | 3.04 | m |
| 30.36 | 2.94 | m |
| 30.70 | 2.91 | w |
| 31.52 | 2.84 | m |
| 31.84 | 2.81 | m |
| 32.62 | 2.74 | m |
| 33.20 | 2.70 | m |
| 33.68 | 2.66 | w |
| 33.98 | 2.64 | w |
| 34.22 | 2.62 | m |
| 34.68 | 2.58 | w |
| 35.04 | 2.56 | m | to the reaction mixture. Next, 1.53 g KOAc (99.4%) was dissolved in 25.00 g de-ionized water and the resulting solution added dropwise to the reaction mixture. Vigorous stirring was required to thin out the reaction mixture. The reaction mixture was distributed among 7 Teflon-lined autoclaves and digested quiescently at temperatures of 95, 125, 150, and 175° C., for either 41 or 172 hr or both at autogenous pressures. The solid products were isolated by centrifugation and washed with de-ionized water. All seven of the products were identified as PST-16, which has the CGS topology, by powder x-ray diffraction. The representative diffraction lines for the 150° C. product digested for 172 hr are shown in Table 7 below. Elemental analysis showed this product was composed of the elemental ratios C/N=5.06, Al/P=0.53, Zn/P=0.48, K/P=0.24, and N/P=0.24, consistent with the stoichiometry ETMA$_{0.24}$K$_{0.24}$Zn$_{0.48}$Al$_{0.53}$P.

TABLE 7

| 2-Θ | d(Å) | I/I$_0$(%) |
|---|---|---|
| 8.20 | 10.78 | vs |
| 10.74 | 8.23 | w |
| 11.58 | 7.64 | m |
| 12.38 | 7.14 | m |
| 13.00 | 6.80 | w |
| 13.24 | 6.68 | w |
| 16.42 | 5.39 | m |
| 16.80 | 5.27 | m |
| 17.12 | 5.17 | w |
| 19.16 | 4.63 | vs |
| 19.38 | 4.58 | vs, sh |
| 19.52 | 4.54 | m |
| 20.56 | 4.32 | w |
| 21.34 | 4.16 | w |
| 21.78 | 4.08 | m |
| 22.16 | 4.01 | m |
| 22.74 | 3.91 | w |
| 23.00 | 3.86 | m |
| 23.26 | 3.82 | m |
| 23.72 | 3.75 | m |
| 24.08 | 3.69 | m |
| 24.80 | 3.59 | m |
| 26.26 | 3.39 | m |
| 26.66 | 3.34 | m |
| 27.18 | 3.28 | m |
| 28.18 | 3.16 | w |
| 28.94 | 3.08 | m |
| 29.32 | 3.04 | m |
| 30.34 | 2.94 | m |
| 30.70 | 2.91 | m |
| 31.52 | 2.84 | m |
| 31.72 | 2.82 | m |
| 32.30 | 2.77 | w |
| 32.74 | 2.73 | w |
| 33.18 | 2.70 | m |
| 33.68 | 2.66 | w |
| 34.22 | 2.62 | m |
| 34.68 | 2.58 | w |
| 35.02 | 2.56 | m |
| 35.58 | 2.52 | w |

Example 8

A Teflon beaker was charged with 130.00 g ETMAOH (20%) and placed under a high speed stirrer. Aluminum isopropoxide (13.3% Al) was pre-ground in a mortar and 6.27 g was dissolved in the ETMAOH solution. Then 21.20 g H$_3$PO$_4$ (85.7%) was added dropwise while stirring continued. Separately, 6.78 g Zn(OAc)$_2$*2H$_2$O was dissolved in 30.39 g de-ionized water. This solution was added dropwise Example 9

A Teflon beaker was charged with 145.00 g diethyldimethylammonium hydroxide (DEDMAOH, 20% aqueous, SACHEM, Inc.) and placed under a high-speed stirring apparatus. Pre-ground aluminum isopropoxide (13.2% Al) was added and dissolved with stirring. This was followed by the fast dropwise addition of 16.69 g H$_3$PO$_4$ (85.7%). Separately, 5.34 g Zn(OAc)$_2$*2H$_2$O was dissolved in 25.00 g de-ionized water. This solution was added to the reaction mixture dropwise and intermittently. An additional solution was prepared by dissolving 1.19 g KOAc (99.4%) in 12.44 g de-ionized water, which was added dropwise to the reaction mixture. The mixture was allowed to stir and then was distributed among 7 Teflon-lined autoclaves which were digested quiescently at temperatures of 95, 125, 150, and 175° C., for either 48 or 181 hr or both at autogenous pressures. The solid products were isolated by centrifugation and washed with de-ionized water. The products isolated from the 181 hr digestions at 95° C. and 125° C. were identified as PST-16, which has the CGS topology, by powder x-ray diffraction. The representative diffraction lines for the product from the 125° C./181 hr digestion are shown in Table 8 below. Elemental analysis showed this product was composed of the elemental ratios C/N=5.42, Al/P=0.48, Zn/P=0.50, K/P=0.26, and N/P=0.25, consistent with the stoichiometry DEDMA$_{0.25}$K$_{0.26}$Zn$_{0.50}$Al$_{0.48}$P.

TABLE 8

| 2-Θ | d(Å) | I/I$_0$(%) |
| --- | --- | --- |
| 8.14 | 10.86 | vs |
| 10.71 | 8.26 | w |
| 11.54 | 7.66 | w |
| 12.25 | 7.22 | m |
| 12.96 | 6.82 | w |
| 13.18 | 6.71 | w |
| 16.28 | 5.44 | m |
| 16.68 | 5.31 | w |
| 17.05 | 5.20 | w |
| 19.10 | 4.64 | m |
| 19.42 | 4.57 | w |
| 21.26 | 4.18 | w |
| 21.52 | 4.13 | m |
| 21.98 | 4.04 | w |
| 22.58 | 3.93 | w |
| 22.88 | 3.88 | m |
| 23.22 | 3.83 | w |
| 23.53 | 3.78 | w |
| 23.88 | 3.72 | m |
| 24.12 | 3.69 | w |
| 24.70 | 3.60 | m |
| 26.18 | 3.40 | m |
| 26.48 | 3.36 | w |
| 26.92 | 3.31 | m |
| 28.07 | 3.18 | w |
| 28.64 | 3.11 | m |
| 29.08 | 3.07 | m |
| 30.15 | 2.96 | w |
| 30.42 | 2.94 | w |
| 30.67 | 2.91 | w |
| 31.14 | 2.87 | w |
| 31.52 | 2.84 | m |
| 32.56 | 2.75 | w |
| 32.86 | 2.72 | w |
| 33.72 | 2.66 | w |
| 34.12 | 2.63 | m |
| 34.78 | 2.58 | w |
| 35.02 | 2.56 | w |

Example 10

A Teflon beaker was charged with 116.00 g DEDMAOH (20%) and placed under a high-speed stirring apparatus. With stirring, the solution was diluted with 25.64 g de-ionized water. Pre-ground aluminum isopropoxide (13.2% Al), 4.97 g, was added and dissolved in the hydroxide solution. This was followed by the dropwise addition of 16.69 g H$_3$PO$_4$ (85.7%). Separately, 5.34 g Zn(OAc)$_2$*2H$_2$O was dissolved in 25.00 g de-ionized water. This solution was added dropwise to the stirring reaction mixture. Another solution was prepared by dissolving 1.19 g KOAc (99.4%) in 25.00 g de-ionized water. This was added dropwise to the reaction mixture while continuing the stirring. The reaction mixture was homogenized further before it was distributed among 7 Teflon-lined autoclaves, which were digested quiescently at temperatures of 95, 125, 150, and 175° C., for either 48 or 170 hr or both at autogenous pressures. The solid products were isolated by centrifugation and washed with de-ionized water. The products isolated from all of the digestions were identified as PST-16, which has the CGS topology, by powder x-ray diffraction. The representative diffraction lines for the product from the 125° C./48 hr digestion are shown in Table 9 below. Elemental analysis showed this product was composed of the elemental ratios C/N=5.53, Al/P=0.49, Zn/P=0.50, K/P=0.25, and N/P=0.23, consistent with the stoichiometry DEDMA$_{0.23}$K$_{0.25}$Zn$_{0.50}$Al$_{0.49}$P.

TABLE 9

| 2-Θ | d(Å) | I/I$_0$(%) |
| --- | --- | --- |
| 8.20 | 10.78 | vs |
| 10.76 | 8.22 | w |
| 11.60 | 7.62 | m |
| 12.33 | 7.17 | m |
| 13.04 | 6.79 | w |
| 13.28 | 6.66 | w |
| 16.38 | 5.41 | m |
| 16.74 | 5.29 | w |
| 17.10 | 5.18 | w |
| 19.20 | 4.62 | m |
| 19.50 | 4.55 | m |
| 20.58 | 4.31 | w |
| 21.34 | 4.16 | w |
| 21.64 | 4.10 | m |
| 22.04 | 4.03 | w |
| 22.30 | 3.98 | w |
| 22.70 | 3.91 | w |
| 22.94 | 3.87 | w |
| 23.28 | 3.82 | w |
| 23.60 | 3.77 | w |
| 23.79 | 3.74 | w |
| 23.96 | 3.71 | m |
| 24.24 | 3.67 | w |
| 24.80 | 3.59 | m |
| 26.26 | 3.39 | m |
| 26.56 | 3.35 | w |
| 27.00 | 3.30 | m |
| 28.12 | 3.17 | w |
| 28.72 | 3.11 | m |
| 29.14 | 3.06 | m |
| 30.24 | 2.95 | w |
| 30.54 | 2.93 | w |
| 30.71 | 2.91 | w |
| 31.22 | 2.86 | w |
| 31.56 | 2.83 | m |
| 32.96 | 2.72 | w |
| 33.78 | 2.65 | w |
| 34.22 | 2.62 | m |
| 34.90 | 2.57 | m |
| 35.12 | 2.55 | m |
| 35.53 | 2.52 | w |

Example 11

A Teflon beaker was charged with 126.33 g ETMAOH (20 wt. %) and placed under a high speed overhead stirrer. This was followed by the addition and dissolution of 6.26 g of Al(OiPr)$_3$ (98+%) with stirring. Then 20.79 g H$_3$PO$_4$ (85%) was added slowly while mixing continued. Separately, 6.73 g of zinc acetate dihydrate was dissolved in 30 g of deionized water. The resulting zinc solution was then slowly added to the Al/P/ETMAOH solution while mixing with an overhead stirrer. In a separate beaker, 1.80 g KBr was dissolved in 58.1 g deionized water. This was then added slowly to the reaction mixture while continuing to mix with an overhead stirrer, resulting in a clear solution. The solution was then divided between 4×125 ml autoclaves and digested quiescently for 4 d at 150° C. at autogenous pressure. The solid products were isolated by centrifugation and washed with de-ionized water. Analysis by powder x-ray diffraction showed that all of the reactions resulted in PST-16 products with the CGS topology. Representative diffraction lines for the product are shown in Table 10 below.

TABLE 10

| 2Θ | d(Å) | I/I$_0$ % |
|---|---|---|
| 8.23 | 10.74 | vs |
| 10.76 | 8.22 | w |
| 11.61 | 7.61 | w |
| 12.53 | 7.06 | vs |
| 13.07 | 6.77 | w |
| 13.29 | 6.66 | w |
| 16.47 | 5.38 | m |
| 16.85 | 5.26 | w |
| 17.19 | 5.15 | w |
| 17.48 | 5.07 | w |
| 19.20 | 4.62 | w |
| 19.46 | 4.56 | w |
| 19.58 | 4.53 | w |
| 21.40 | 4.15 | m |
| 21.47 | 4.13 | m |
| 21.59 | 4.11 | m |
| 21.83 | 4.07 | w |
| 22.23 | 4.00 | w |
| 22.76 | 3.90 | w |
| 23.05 | 3.86 | w |
| 23.31 | 3.81 | w |
| 23.77 | 3.74 | w |
| 24.15 | 3.68 | w |
| 24.83 | 3.58 | w |
| 26.29 | 3.39 | w |
| 26.70 | 3.34 | w |
| 27.26 | 3.27 | m |
| 27.92 | 3.19 | m |
| 28.22 | 3.16 | m |
| 28.98 | 3.08 | m |
| 29.39 | 3.04 | w |
| 30.39 | 2.94 | w |
| 30.71 | 2.91 | w |
| 31.59 | 2.83 | w |
| 31.83 | 2.81 | w |
| 32.35 | 2.76 | w |
| 32.63 | 2.74 | w |
| 32.79 | 2.73 | w |
| 33.25 | 2.69 | m |
| 33.41 | 2.68 | m |
| 33.71 | 2.66 | w |
| 34.03 | 2.63 | w |
| 34.27 | 2.61 | w |
| 34.63 | 2.59 | w |

Example 12

A Teflon beaker was charged with 120.00 g Tetraethylammonium hydroxide (TEAOH, 35%, SACHEM Inc.) and placed under a high speed overhead stirrer. Pre-ground aluminum isopropoxide (13.3% Al, Sigma-Aldrich), 5.79 g, was dissolved in the TEAOH solution. This was followed by the fast dropwise addition of 19.57 g H$_3$PO$_4$ (85.7%). The reaction mixture was diluted with 37.65 g de-ionized water. Separately, a zinc acetate solution was prepared by dissolving 6.26 g Zn(OAc)$_2$*2H$_2$O in 35.00 g de-ionized water. This solution was added in a fast dropwise manner to the reaction mixture with vigorous stirring. Then a solution was prepared by dissolving 1.41 g potassium acetate, KOAc (99.4%), in 25.00 g de-ionized water. This solution was also added fast dropwise to the reaction mixture, resulting in a clear solution. The reaction mixture was distributed among 7 Teflon-lined autoclaves which were digested quiescently at 95, 125, 150 and 175° C. for either 59 or 159 hr at autogenous pressure. The solid products were isolated by centrifugation, washed with de-ionized water and dried at room temperature. The major product in every case was determined by x-ray diffraction to be PST-19, which has the SBS topology, with most of the reactions yielding products showing no impurities. Representative x-ray diffraction lines are listed for the PST-19 product resulting from the 125° C./159 hr reaction in table 11 below. Analysis by Scanning Electron Microscopy (SEM) showed the PST-19 product to consist of extremely thin plate crystals, with the plate face diameters ranging from about 0.3 to about 1µ across while plate thicknesses are on the order of 0.01 to about 0.1µ. Elemental analysis yielded the stoichiometry TEA$_{0.05}$K$_{0.33}$Al$_{0.51}$Zn$_{0.62}$P for the PST-19 product.

TABLE 11

| 2-Θ | d(Å) | I/I$_0$(%) |
|---|---|---|
| 5.78 | 15.28 | w |
| 6.50 | 13.59 | vs |
| 10.00 | 8.83 | w |
| 11.94 | 7.40 | w |
| 13.14 | 6.73 | w |
| 15.32 | 5.78 | w |
| 15.60 | 5.68 | w |
| 16.53 | 5.36 | w |
| 20.04 | 4.43 | m |
| 20.94 | 4.24 | w |
| 21.98 | 4.04 | m |
| 22.14 | 4.01 | w |
| 23.98 | 3.71 | w |
| 25.78 | 3.45 | w |
| 26.66 | 3.34 | m |
| 27.78 | 3.21 | w |
| 28.24 | 3.16 | m |
| 29.14 | 3.06 | w |
| 31.20 | 2.86 | m |
| 35.20 | 2.55 | w |

Example 13

A Teflon beaker was charged with 928.44 g of Triethylpropylammonium hydroxide (TEPAOH, 19.7%, SACHEM Inc.) followed by the addition 27.96 g of aluminum tri-sec-butoxide (Sigma Aldrich, 97+%), which were then homogenized with a high speed overhead stirrer to make a clear solution. Then 78.50 g of H$_3$PO$_4$ (85%) was slowly add to the mixture. Separately, 24.91 g of Zn(OAc)$_2$*2H$_2$O was dissolved in 60 g de-ionized water and then was added dropwise to the reaction mixture with vigorous mixing. Similarly, 2.12 g of KCl was dissolved in 10.00 g de-ionized water and added drop-wise to the stirring reaction mixture. The reaction mixture was further homogenized until it was a clear solution. A portion of the solution, 1050 g, was placed in a 2-L Teflon-lined PARR reactor and digested quiescently for 92 hours at 175° C. at autogenous pressure. The solid product was isolated by centrifugation, washed with de-ionized water and dried at room temperature. Characterization via powder x-ray diffraction showed that the product was PST-19 with the SBS topology. Representative diffraction lines observed for the product are provided below in table 12. The FIGURE shows that analysis by SEM showed the product to consist of hexagonal plate crystals with dimensions across the face of the plate ranging from 0.2 to about 2µ, while the plate thickness is less than about 0.1µ.

Elemental analysis yielded the stoichiometry TEPA$_{0.18}$K$_{0.22}$Zn$_{0.63}$Al$_{0.43}$P for the PST-19 product.

TABLE 12

| 2-Θ | d(Å) | I/I$_0$(%) |
|---|---|---|
| 5.92 | 14.93 | w |
| 6.69 | 13.20 | vs |
| 10.15 | 8.71 | w |
| 11.40 | 7.76 | w |
| 11.68 | 7.57 | w |
| 12.10 | 7.31 | w |
| 13.22 | 6.69 | w |
| 15.43 | 5.74 | w |
| 15.77 | 5.61 | w |
| 16.62 | 5.33 | w |
| 18.70 | 4.74 | w |
| 20.22 | 4.39 | w |
| 21.06 | 4.22 | w |
| 21.97 | 4.04 | w |
| 22.21 | 4.00 | w |
| 24.13 | 3.69 | w |
| 25.71 | 3.46 | w |
| 25.85 | 3.44 | w |
| 26.46 | 3.37 | w |
| 26.77 | 3.33 | w |
| 28.38 | 3.14 | w |
| 29.29 | 3.05 | w |
| 29.92 | 2.98 | w |
| 30.44 | 2.93 | w |
| 31.35 | 2.85 | w |
| 32.83 | 2.73 | w |
| 35.32 | 2.54 | w |

Example 14

A Teflon beaker was charged with 81.72 g of Diethylmethylpropylammonium hydroxide (DEMPAOH, 20.7%, SACHEM Inc.) followed by the addition of 2.83 g of aluminum-tri-sec-butoxide (97+%), which were then homogenized with a high speed overhead stirrer to make a clear solution. Then 7.96 g H$_3$PO$_4$ (85%) was slowly added to the mixture as stirring continued. Separately, 2.53 g Zn(OAc)$_2$*2H$_2$O was dissolved in 8.00 g de-ionized water. This solution was added to the reaction mixture in a dropwise fashion. Next, a solution was prepared by dissolving 0.43 g KCl in 4.00 g de-ionized water. This solution was also added dropwise to the reaction mixture with vigorous stirring. The resulting clear solution was distributed among three Teflon-lined autoclaves that were rotated in a rotisserie oven as they were digested at 175° C. for 48, 72, and 96 hr at autogenous pressure. The products were isolated by centrifugation, washed with de-ionized water, and dried at 100° C. The products were identified as PST-19 with the SBS topology by powder x-ray diffraction. Representative diffraction lines are shown for the products in Table 13A (48 hr product) and Table 13B (96 hr product). Elemental analysis on the product from the 48 hr digestion yielded the stoichiometry DEMPA$_{0.19}$K$_{0.26}$Al$_{0.45}$Zn$_{0.57}$P for the PST-19 product.

TABLE 13

| Table 13A | | | Table 13B | | |
|---|---|---|---|---|---|
| 2-Θ | d(Å) | I/I$_0$(%) | 2-Θ | d(Å) | I/I$_0$(%) |
| 5.85 | 15.09 | w | 5.93 | 14.88 | w |
| 6.51 | 13.56 | vs | 6.63 | 13.32 | vs |
| 10.08 | 8.77 | w | 10.13 | 8.73 | w |
| 11.66 | 7.58 | w | 11.71 | 7.55 | w |
| 12.02 | 7.36 | w | 12.11 | 7.30 | w |
| 13.08 | 6.77 | w | 13.20 | 6.70 | w |
| 15.37 | 5.76 | w | 15.49 | 5.72 | w |
| 15.69 | 5.64 | w | 15.75 | 5.62 | w |
| 16.49 | 5.37 | w | 16.61 | 5.33 | w |
| 18.64 | 4.76 | w | 18.70 | 4.74 | w |
| 20.14 | 4.41 | w | 20.22 | 4.39 | w |
| 20.46 | 4.34 | w | 21.11 | 4.20 | w |
| 21.00 | 4.23 | w | 21.95 | 4.05 | w |
| 21.94 | 4.05 | w | 24.15 | 3.68 | w |
| 24.05 | 3.70 | w | 25.84 | 3.44 | w |
| 25.67 | 3.47 | w | 26.40 | 3.37 | w |
| 26.34 | 3.38 | w | 26.82 | 3.32 | w |
| 26.72 | 3.33 | w | 27.66 | 3.22 | w |
| 27.72 | 3.22 | w | 28.34 | 3.15 | w |
| 28.22 | 3.16 | w | 29.30 | 3.05 | w |
| 29.22 | 3.05 | w | 29.91 | 2.98 | w |
| 29.84 | 2.99 | w | 30.47 | 2.93 | w |
| 30.45 | 2.93 | w | 31.33 | 2.85 | w |
| 31.23 | 2.86 | w | 35.34 | 2.54 | w |
| 35.22 | 2.55 | w | | | |

Example 15

A Teflon beaker was charged with 77.36 g of dimethylethylpropylammonium hydroxide (DMEPAOH, SACHEM Inc., 20.0%) and placed under a high-speed overhead stirrer. Then 2.87 g aluminum tri-sec-butoxide (97+%) was added with stirring, easily dissolving within minutes. This was followed by the dropwise addition of 8.05 g of H$_3$PO$_4$ (85%). Separately, Zn(OAc)$_2$*2H$_2$O, 2.55 g, was dissolved in 8.00 g de-ionized water. This solution was added dropwise to the stirring reaction mixture. Next, KCl, 0.43 g, was dissolved in 4.00 g de-ionized water and added dropwise with continued stirring. Continued homogenization of the reaction mixture produced a clear solution. The final reaction mixture was distributed among (3) Teflon-lined autoclaves that were rotated in a rotisserie oven as they were digested at 175° C. for periods of 48, 72 and 96 hr at autogenous pressure. The products were isolated by centrifugation, washed with de-ionized water and dried at 100° C. The products were identified as PST-19 with the SBS topology via powder x-ray diffraction. Representative diffraction lines are given for the products from the 48 and 96 hr digestions in Tables 14A and 14B, respectively. Elemental analysis on the product digested for 48 hr yielded the stoichiometry DMEPA$_{0.20}$K$_{0.31}$Zn$_{0.58}$Al$_{0.44}$P for the PST-19 product.

TABLE 14

| Table 14A | | | Table 14B | | |
|---|---|---|---|---|---|
| 2-Θ | d(Å) | I/I$_0$(%) | 2-Θ | d(Å) | I/I$_0$(%) |
| 5.81 | 15.20 | w | 5.89 | 14.99 | m |
| 6.47 | 13.65 | vs | 6.55 | 13.48 | vs |
| 10.01 | 8.83 | w | 10.12 | 8.73 | w |
| 11.61 | 7.61 | w | 11.66 | 7.58 | w |
| 11.96 | 7.40 | w | 12.04 | 7.35 | w |
| 13.10 | 6.76 | w | 13.08 | 6.77 | w |
| 15.31 | 5.78 | w | 13.41 | 6.60 | w |
| 15.65 | 5.66 | w | 15.41 | 5.75 | w |
| 16.51 | 5.37 | w | 15.77 | 5.62 | w |
| 18.60 | 4.77 | w | 16.59 | 5.34 | w |
| 20.08 | 4.42 | w | 18.68 | 4.75 | w |
| 20.80 | 4.27 | w | 20.18 | 4.40 | w |

TABLE 14-continued

| Table 14A | | | Table 14B | | |
|---|---|---|---|---|---|
| 2-Θ | d(Å) | I/I₀(%) | 2-Θ | d(Å) | I/I₀(%) |
| 21.99 | 4.04 | w | 20.61 | 4.31 | w |
| 23.21 | 3.83 | w | 21.02 | 4.22 | w |
| 23.97 | 3.71 | w | 21.88 | 4.06 | w |
| 25.58 | 3.48 | w | 24.11 | 3.69 | w |
| 26.78 | 3.33 | w | 25.67 | 3.47 | w |
| 28.18 | 3.16 | w | 26.80 | 3.32 | w |
| 29.17 | 3.06 | w | 27.64 | 3.22 | w |
| 31.17 | 2.87 | w | 28.32 | 3.15 | w |
| 35.24 | 2.54 | w | 29.26 | 3.05 | w |
| | | | 30.39 | 2.94 | w |
| | | | 31.15 | 2.87 | w |
| | | | 31.37 | 2.85 | w |
| | | | 32.83 | 2.73 | w |
| | | | 34.76 | 2.58 | w |
| | | | 35.23 | 2.55 | w |

Examples 16-18

Examples 16-18 cover the synthesis of the cyclic diquat structure directing agents SDA1, SDA2 and SDA3 that are utilized in the Charge Density Mismatch syntheses of MeAPO-81 in examples 19-21.

Example 16 Synthesis of SDA1

N,N,N',N'-tetramethyl-N,N'-p-xyleno-1,6-hexanediammonium dibromide

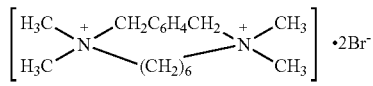

A 50.00 g portion of α,α'dibromo-p-xylene (Sigma-Aldrich) was placed in a 1-liter beaker and dissolved in 550 ml dry tetrahydrofuran (THF) using a stirbar. The resulting solution was transferred to a 1 liter 3-neck round bottom flask equipped with an overhead stirrer, a heating mantle and a reflux condenser. Separately, 33.31 g N,N,N',N'-tetramethyl-1,6-hexanediamine (99%, Sigma-Aldrich) was diluted with 32.50 g THF and placed in a pressure-equalizing dropping funnel that was attached to one of the necks of the round bottom flask. The amine solution was then added to the dibromide solution in the flask dropwise with stirring. Some solid formation was observed during the addition. Upon completion of the addition, the dropping funnel was removed and a thermocouple connected to a temperature controller was inserted into the flask. After stirring for 15 minutes, the reaction mixture was heated to 64° C. and held at that temperature for 42 hr. The reaction was allowed to cool and the solid product was isolated by filtration under a nitrogen blanket. The solid was washed with ether and filtered under nitrogen blanket before residual solvent was removed using a vacuum oven. The identity of cyclic diquat SDA1, N,N,N',N'-tetramethyl-N,N'-p-xyleno-1,6-hexanediammonium dibromide, in which two dimethyl-substituted quaternized N-atoms are attached by 1) a $(CH_2)_6$ chain and 2) a p-xylyl group, was confirmed by $^{13}C$ nmr as there was excellent agreement between observed and calculated nmr line positions.

Example 17 Synthesis of SDA2

N,N,N',N'-tetramethyl-N,N'-butano-1,6-hexanediammonium dibromide

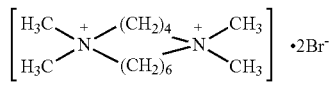

A 85.00 g portion of N,N,N',N'-tetramethyl-1,6-hexanediamine (99%) was diluted in 500 ml dry tetrahydrofuran (THF) in a 1-liter beaker using a stirbar. The resulting solution was transferred to a 1 liter 3-neck round bottom flask equipped with an overhead stirrer, a heating mantle and a reflux condenser. Separately, 106.51 g 1,4-dibromobutane (99.1%, Sigma-Aldrich) was placed in a pressure-equalizing dropping funnel that was attached to one of the necks of the round bottom flask. The dibromide was then added to the amine solution in the flask in a dropwise fashion with stirring. The reaction mixture remained a solution over the course of the addition. Upon completion of the addition, the dropping funnel was removed and a thermocouple connected to a temperature controller was inserted into the flask. After stirring for 30 minutes, there was no visible reaction, the reaction mixture was still a solution. The reaction mixture was heated to 64° C. and held at that temperature for 24 hr. Solid formation in the reaction mixture started to become visible once the reaction reached 40° C. Once completed, the reaction was allowed to cool and the solid product was isolated by filtration under a nitrogen blanket. The solid was washed with ether and filtered under nitrogen blanket before residual solvent was removed using a vacuum oven. The identity of cyclic diquat SDA2, N,N,N',N'-tetramethyl-N,N'-butano-1,6-hexanediammonium dibromide, in which two dimethyl-substituted quaternized N-atoms are attached by 1) a $(CH_2)_6$ chain and 2) a $(CH_2)_4$ chain, was confirmed by $^{13}C$ nmr as there was excellent agreement between observed and calculated nmr line positions.

Example 18 Synthesis of SDA3

N,N,N',N'-tetramethyl-N,N'-hexano-1,6-hexanediammonium dibromide

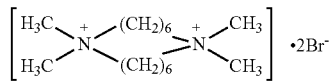

A 60.00 g portion of 1,6-dibromohexane (96%, Sigma-Aldrich) was placed in a 1-liter beaker and dissolved in 500 ml dry tetrahydrofuran (THF) using a stirbar. The resulting solution was transferred to a 1 liter 3-neck round bottom flask equipped with an overhead stirrer, a heating mantle and a reflux condenser. Separately, 41.09 g N,N,N',N'-tetramethyl-1,6-hexanediamine (99%, Sigma-Aldrich) was diluted with 50 ml THF and placed in a pressure-equalizing dropping funnel that was attached to one of the necks of the round bottom flask. The amine solution was then added to the dibromide solution in the flask dropwise, but quickly, with stirring, resulting in a clear solution. Upon completion of the addition, the dropping funnel was removed and a thermocouple connected to a temperature controller was inserted into the flask. The reaction mixture was then heated to 64° C. and held at that temperature for 21 hr. The final reaction mixture consisted of a voluminous white solid suspended in the liquid. The reaction was allowed to cool and the solid product was isolated by filtration under a nitrogen blanket. The solid was washed with ether and filtered under nitrogen blanket before residual solvent was removed using a vacuum oven. The identity of cyclic diquat SDA3, in which two dimethyl-substituted quaternized N-atoms are attached to each other by 1) a $(CH_2)_6$ chain and 2) another $(CH_2)_6$ chain, was confirmed by $^{13}C$ nmr as there was excellent agreement between observed and calculated nmr line positions.

Example 19

A Teflon beaker was charged with 130.00 g tetrapropylammonium hydroxide (TPAOH, 40%, SACHEM Inc.) and placed under a high speed overhead stirrer. Then pre-ground aluminum isopropoxide (Sigma-Aldrich, 13.2% Al), 5.23 g was added and dissolved with stirring. Then 17.54 g $H_3PO_4$ (85.7%) was added dropwise to the reaction mixture with continued stirring, yielding a clear solution. Separately, 5.61 g $Zn(OAc)_2 \cdot 2H_2O$ (Sigma-Aldrich) was dissolved in 25.00 g deionized water. This solution was added fast dropwise to the reaction mixture with stirring, forming a clear solution within five minutes. The reaction mixture was diluted further with 15.00 g deionized water. Separately, 5.58 g of the cyclic diquat SDA1 from example 15 was dissolved in 33.00 g deionized water. This was added dropwise to the reaction mixture, which induced solid formation immediately and formed a white suspension by the end of the addition. Separately, KOAc (Sigma-Aldrich, 99.4%), 1.26 g, was dissolved in 10.00 g de-ionized water. This solution was added dropwise to the white gel/suspension. The reaction mixture was distributed among seven Teflon-lined autoclaves, which were digested quiescently at 95, 125, 150, and 175° C. for either 66 or 189 hr at autogenous pressure. The solid products were isolated by centrifugation, washed with deionized water and dried at room temperature. All of the reactions yielded MeAPO-81 products with the BPH topology as determined by powder x-ray diffraction. Representative x-ray diffraction lines observed for the 175° C./189 hr product are given in Table 15. Scanning Electron Microscopic (SEM) analysis of this product showed the crystals to consist of thin rounded hexagonal plates, 0.2-0.8μ across and less than about 100 nm thick. Elemental analysis on this same product yielded the stoichiometry $N_{0.31}K_{0.24}Zn_{0.51}Al_{0.51}P$.

TABLE 15

| 2-Θ | d(Å) | I/I₀(%) |
|---|---|---|
| 6.70 | 13.18 | s |
| 7.56 | 11.69 | vs |
| 10.08 | 8.77 | w |
| 13.12 | 6.74 | m |
| 13.40 | 6.60 | m |
| 14.74 | 6.00 | w |
| 15.07 | 5.88 | w |
| 15.40 | 5.75 | m |
| 16.55 | 5.35 | w |
| 18.82 | 4.71 | m |
| 20.22 | 4.39 | s |
| 21.18 | 4.19 | s |
| 23.82 | 3.73 | m |
| 24.14 | 3.68 | vs |
| 26.54 | 3.36 | m |

TABLE 15-continued

| 2-Θ | d(Å) | I/I₀(%) |
|---|---|---|
| 27.26 | 3.27 | m |
| 27.46 | 3.24 | w |
| 28.30 | 3.15 | m |
| 28.62 | 3.12 | m |
| 29.70 | 3.01 | m |
| 30.16 | 2.96 | m |
| 30.56 | 2.92 | m |
| 33.36 | 2.68 | m |
| 33.90 | 2.64 | m |
| 35.12 | 2.55 | m |
| 36.58 | 2.45 | w |
| 38.12 | 2.36 | w |
| 38.88 | 2.31 | w |
| 40.02 | 2.25 | w |
| 40.86 | 2.21 | w |
| 43.02 | 2.10 | m |

Example 20

A Teflon beaker was charged with 130.00 g tetrapropylammonium hydroxide (TPAOH, 40%, SACHEM Inc.) and placed under a high speed overhead stirrer. Then pre-ground aluminum isopropoxide (Sigma-Aldrich, 13.2% Al), 5.23 g was added and dissolved with stirring. Then 17.54 g $H_3PO_4$ (85.7%) was added dropwise to the reaction mixture with continued stirring, yielding a clear solution. Separately, 5.61 g $Zn(OAc)_2 \cdot 2H_2O$ (Sigma-Aldrich) was dissolved in 25.00 g deionized water. This solution was added fast dropwise to the reaction mixture with stirring, forming a clear solution within five minutes. The reaction mixture was diluted further with 15.00 g deionized water. Separately, 4.96 g of the cyclic diquat SDA2 from example 16 was dissolved in 33.00 g deionized water. This was added dropwise to the reaction mixture, which induced solid formation immediately and formed a white suspension by the end of the addition. Separately, KOAc (Sigma-Aldrich, 99.4%), 1.26 g, was dissolved in 10.00 g de-ionized water. This solution was added dropwise to the white gel/suspension. The reaction mixture was distributed among seven Teflon-lined autoclaves, which were digested quiescently at 95, 125, 150, and 175° C. for either 66 or 188 hr at autogenous pressure. The solid products were isolated by centrifugation, washed with deionized water and dried at room temperature. Powder x-ray diffraction showed all products contained MeAPO-81 with the BPH topology as the major product and several of the products were pure MeAPO-81. Representative x-ray diffraction lines are presented for the pure MeAPO-81 product isolated from the 150° C./66 hr digestion in Table 16 below. Elemental analysis performed on this same sample yielded the stoichiometry $N_xK_{0.22}Zn_{0.52}Al_{0.47}P$.

TABLE 16

| 2-Θ | d(Å) | I/I₀(%) |
|---|---|---|
| 6.76 | 13.07 | m |
| 7.64 | 11.57 | vs |
| 10.08 | 8.76 | w |
| 13.17 | 6.71 | m |
| 14.82 | 5.97 | w |
| 15.42 | 5.74 | m |
| 16.63 | 5.33 | w |
| 18.88 | 4.70 | w |
| 20.16 | 4.40 | m |
| 21.22 | 4.18 | s |
| 23.86 | 3.73 | m |
| 24.24 | 3.67 | s |

TABLE 16-continued

| 2-Θ | d(Å) | I/I₀(%) |
|---|---|---|
| 26.58 | 3.35 | m |
| 27.34 | 3.26 | m |
| 27.54 | 3.24 | m |
| 28.46 | 3.13 | w |
| 29.76 | 3.00 | m |
| 30.26 | 2.95 | m |
| 30.64 | 2.92 | m |
| 30.74 | 2.91 | m |
| 33.45 | 2.68 | m |
| 34.02 | 2.63 | m |
| 35.21 | 2.55 | w |

Example 21

A 3 liter beaker was charged with 1000.00 g TPAOH (40%) and placed under a high speed overhead stirrer. Pre-ground aluminum isopropoxide (13.2% Al), 40.21 g, was added and dissolved with stirring. The reaction mixture was then diluted with 600.00 g de-ionized water. Then 134.97 g $H_3PO_4$ (85.7%) was added in a single slow pour with stirring, followed by the addition of 50.00 g de-ionized water. Separately, 43.18 g $Zn(OAc)_2 \cdot 2H_2O$ was dissolved in 173.84 g de-ionized water. This solution was added to the reaction mixture in a dropwise fashion intermittently with vigorous stirring. With continued homogenization, a clear solution results. The final solution weight was 2012.1 g.

A 180.00 g portion of this TPA⁺-Zn—Al—P solution was placed in a Teflon beaker positioned under a high speed overhead stirrer. Separately, 0.86 g KOAc (99.4%) and 7.33 g SDA3 from Example 17 were dissolved in 45.00 g de-ionized water. This solution was added to the reaction mixture dropwise, inducing solid formation with the first few drops. By the end of the addition the reaction mixture was an opaque white gel suspension. The reaction mixture was distributed among seven Teflon-lined autoclaves, which were digested quiescently at 95, 125, 150, and 175° C. for either 52 or 167 hr at autogenous pressure. The solid products were isolated by centrifugation, washed with deionized water and dried at room temperature. Powder x-ray diffraction showed all products contained MeAPO-81 with the BPH topology as the major product and all of the products synthesized at 150 and 175° C. were pure MeAPO-81. Representative x-ray diffraction lines are given in Table 17 below for the product resulting from the 175° C./52 hr digestion. Elemental analysis showed this same material to have the stoichiometry $N_{0.32}K_{0.26}Zn_{0.58}Al_{0.45}P$.

TABLE 17

| 2-Θ | d(Å) | I/I₀(%) |
|---|---|---|
| 6.70 | 13.18 | s |
| 7.54 | 11.72 | vs |
| 10.06 | 8.78 | w |
| 13.06 | 6.77 | w |
| 13.39 | 6.61 | w |
| 14.71 | 6.02 | w |
| 15.40 | 5.75 | m |
| 16.51 | 5.36 | w |
| 18.76 | 4.73 | m |
| 20.00 | 4.44 | m |
| 20.16 | 4.40 | m |
| 21.10 | 4.21 | m |
| 23.72 | 3.75 | w |
| 24.1 | 3.69 | s |
| 26.47 | 3.36 | m |
| 27.14 | 3.28 | w |

TABLE 17-continued

| 2-Θ | d(Å) | I/I₀(%) |
|---|---|---|
| 27.38 | 3.26 | w |
| 28.20 | 3.16 | w |
| 28.54 | 3.13 | m |
| 29.60 | 3.02 | m |
| 30.09 | 2.97 | m |
| 30.44 | 2.93 | m |
| 33.22 | 2.69 | m |
| 33.82 | 2.65 | m |
| 34.98 | 2.56 | w |
| 35.67 | 2.51 | w |
| 36.46 | 2.46 | w |
| 37.97 | 2.37 | w |
| 39.66 | 2.27 | w |
| 40.64 | 2.22 | w |
| 42.84 | 2.11 | w |
| 43.36 | 2.09 | w |
| 49.40 | 1.84 | w |
| 50.15 | 1.82 | w |

The invention claimed is:

1. A microporous crystalline metallophosphate material having a three-dimensional framework of $[M^{2+}O_{4/2}]^{2-}$, $[EO_{4/2}]^-$ and $[PO_{4/2}]^+$ and tetrahedral units and an empirical composition in the as synthesized form and on an anhydrous basis expressed by an empirical formula of:

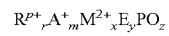

$$R^{p+}_r A^+_m M^{2+}_x E_y PO_z$$

where R is at least one of any quaternary ammonium cation, diquaternary ammonium cation triquaternary ammonium cation, quatroquaternary ammonium cation and mixtures thereof, "r" is the mole ratio of R to P and has a value of about 0.04 to about 1.0, "p" is the weighted average valence of R and varies from 1 to 4, A is an alkali metal selected from the group consisting of Li⁺, Na⁺, K⁺, Rb⁺ and Cs⁺ and mixtures thereof, "m" is the mole ratio of A to P and varies from 0.1 to 1.0, M is a divalent element selected from the group of Zn, Mg, Co, Mn and mixtures thereof, "x" is the mole ratio of M to P and varies from 0.2 to about 0.9, E is a trivalent element selected from the group consisting of aluminum and gallium and mixtures thereof, "y" is the mole ratio of E to P and varies from 0.1 to about 0.8 and "z" is the mole ratio of O to P and has a value determined by the equation:

$$z=(m+p \cdot r+2 \cdot x+3 \cdot y+5)/2$$

and is characterized by a specific x-ray diffraction pattern.

2. The metallophosphate material of claim 1 where E is aluminum.

3. The metallophosphate material of claim 1 where E is gallium.

4. The metallophosphate material of claim 1 where R is at least one quaternary ammonium cation selected from the group consisting of tetramethylammonium (TMA⁺), ethyltrimethylammonium (ETMA⁺), propyltrimethylammonium (PTMA⁺), isopropyltrimethylammonium, diethyldimethylammonium (DEDMA⁺), trimethylbutylammonium (TMBA⁺), methyltriethylammonium (MTEA⁺), propylethyldimethylammonium (PEDMA⁺), N,N-dimethylpiperidinium, N,N-dimethyl-3,5-dimethylpiperidinium, dipropyldimethylammonium (DPDMA⁺), diethylmethylpropylammonium, trimethylpentylammonium (TMPA⁺), dimethyldiisopropylammonium, tetraethylammonium (TEA⁺), hexyltrimethylammonium (HTMA⁺), methylethyldipropylammonium, triethylpropylammonium, dibutyldimethylammonium, benzyltrimethylammonium (BzTMA⁺), diethyldipropylammonium, octyltrimethylammonium, tetrapropylammonium (TPA⁺), decyltrimethylammonium, adamantyltrimethylammonium, methyltributylammonium, dodecyltrimethylammonium, hexadecyltrimethylammonium, tetrabutylammonium (TBA$^+$) and mixtures thereof.

5. The metallophosphate material of claim 1 where R is at least one diquaternary ammonium cation selected from the group consisting of methylene-bis-(trimethylammonium), bis-1,2-(trimethylammonium)ethylene, bis-1,3(trimethylammonium)propane, bis-1,3-(trimethylammonium)-2-propanol, bis-1,4-(trimethylammonium)butane, bis-1,5-(trimethylammonium)pentane (i.e., pentamethonium), bis-1,6-(trimethylammonium)hexane (i.e., hexamethonium, HM$^{2+}$), bis-1,8-(trimethylammonium)octane, bis-1,10-(trimethylammonium)decane, bis-1,5-(triethylammonium)pentane (i.e., pentaethonium), bis-1,6-(triethylammonium)hexane (i.e., hexaethonium), bis-α,α'-(dimethylethylammonium)-p-xylene, bis-α,α'-(dimethylethylammonium)-m-xylene, bis-α,α'-(dimethylethylammonium)-o-xylene, bis-1,5-(N-methylpiperidinum)pentane and bis-1,6-(N-methylpiperidinum)hexane, N,N,N',N'-tetramethyl-N,N'-p-xyleno-1,6-hexanediammonium, N,N,N',N'-tetramethyl-N,N'-butano-1,6-hexanediammonium, N,N,N',N'-tetramethyl-N,N'-hexano-1,6-hexanediammonium, N,N,N',N'-tetraethyl-N,N'-hexano-1,5-pentanediammonium, N,N,N',N'-tetramethyl-N,N'-m-xyleno-1,6-hexanediammonium, N,N,N',N'-tetramethyl-N,N'-o-xyleno-1,2-ethylenediammonium, N,N,N',N'-tetramethyl-N,N'-butano-1,2-ethylenediammonium, N,N,N',N'-tetramethyl-N,N'-hexano-1,2-ethylenediammonium and mixtures thereof.

6. The metallophosphate material of claim 1 where R is at least one triquaternary ammonium cation selected from the group consisting of tris-1,3,5-(triethylammoniomethyl)benzene, tris-1,3,5-(trimethylammoniomethyl)benzene, tris-1,3,5-(dimethylethylammoniomethyl)benzene and mixtures thereof.

7. The metallophosphate material of claim 1 where R is at least one quatroquaternary ammonium cation selected from the group consisting of [(C$_6$H$_5$CH$_2$)(Me$_2$)N(—CH$_2$CH(OH)CH$_2$N(Me$_2$)—)$_3$CH$_2$C$_6$H$_5$]$^{4+}$ (i.e., dibenzylquatroquat), tetrakis-1,2,4,5-(trimethylammoniomethyl)benzene, tetrakis-1,2,4,5-(triethylammoniomethyl)benzene, tetrakis-1,2,4,5-(dimethylethylammoniomethyl)benzene and mixtures thereof.

* * * * *